(12) United States Patent
Burke et al.

(10) Patent No.: US 12,176,069 B2
(45) Date of Patent: Dec. 24, 2024

(54) SYSTEMS AND METHODS FOR DETERMINING PATTERN OF INHERITANCE IN EMBRYOS

(71) Applicant: CooperSurgical, Inc., Trumbull, CT (US)

(72) Inventors: John Burke, Reno, NV (US); Brian Rhees, Reno, NV (US); Joshua David Blazek, Houston, TX (US); Michael Jon Large, Houston, TX (US)

(73) Assignee: CooperSurgical, Inc., Trumbull, CT (US)

( * ) Notice: Subject to any disclaimer, the term of this patent is extended or adjusted under 35 U.S.C. 154(b) by 1224 days.

(21) Appl. No.: 16/907,074

(22) Filed: Jun. 19, 2020

(65) Prior Publication Data

US 2021/0020265 A1 Jan. 21, 2021

Related U.S. Application Data

(60) Provisional application No. 62/865,130, filed on Jun. 21, 2019.

(51) Int. Cl.
*G16B 30/10* (2019.01)
*G16B 20/10* (2019.01)
(Continued)

(52) U.S. Cl.
CPC .............. *G16B 30/10* (2019.02); *G16B 20/10* (2019.02); *G16B 20/20* (2019.02); *C12Q 1/6883* (2013.01);
(Continued)

(58) Field of Classification Search
CPC ........ G16B 30/10; G16B 20/10; G16B 20/20; G16B 10/00; C12Q 1/6883; C12Q 2600/156
See application file for complete search history.

(56) References Cited

U.S. PATENT DOCUMENTS 8,934,098 B2   1/2015   Cox et al.
10,113,196 B2 *   10/2018   Ryan ................... C12Q 1/6869
(Continued)

FOREIGN PATENT DOCUMENTS

JP   2014-507141   3/2014
WO   WO 2006/084132 A2   8/2006
(Continued)

OTHER PUBLICATIONS

Reinert et al., "Alignment of Next-Generation Sequencing Reads," Annu. Rev. Genomics Hum. Genet., May 2015, 22 pages.
(Continued)

*Primary Examiner* — Jesse P Frumkin
(74) *Attorney, Agent, or Firm* — Fish & Richardson P.C.

(57) ABSTRACT

A method for determining pattern of inheritance in an embryo for a region of interest is provided, comprising receiving embryo, maternal and paternal sequence data; aligning the received sequence data to a reference genome; identifying a region of interest in the aligned embryo sequence data; identifying single nucleotide polymorphisms (SNPs) in the maternal sequence data, paternal sequence data, and the identified region of interest in the embryo sequence data; imputing missing gaps in the maternal sequence data and the paternal sequence data using an imputation reference; counting the number of SNPs that are common between the embryo and the mother/father in the identified region of interest for the embryo sequence data and a corresponding region on the maternal/paternal sequence data to determine a maternal/paternal contribution value; and classifying a pattern of inheritance for the embryo as maternal or paternal based on the relative contribution values between mother and father.

14 Claims, 17 Drawing Sheets

(51) Int. Cl.
  *G16B 20/20* (2019.01)
  *C12Q 1/6883* (2018.01)
  *G16B 10/00* (2019.01)
(52) U.S. Cl.
  CPC ........ *C12Q 2600/156* (2013.01); *G16B 10/00* (2019.02)

(56) References Cited

U.S. PATENT DOCUMENTS

| | | | |
|---|---|---|---|
| 2011/0124111 | A1 | 5/2011 | Hoshizaki et al. |
| 2012/0196754 | A1* | 8/2012 | Quake .................. C12Q 1/6881 435/287.2 |
| 2013/0029852 | A1 | 1/2013 | Rava |
| 2013/0085681 | A1 | 4/2013 | Deciu et al. |
| 2013/0261984 | A1 | 10/2013 | Eberle |
| 2013/0288244 | A1 | 10/2013 | Deciu |
| 2013/0304392 | A1 | 11/2013 | Deciu et al. |
| 2015/0100244 | A1 | 4/2015 | Hannum |
| 2016/0019338 | A1* | 1/2016 | Chudova .............. C12Q 1/6858 702/20 |
| 2016/0108475 | A1 | 4/2016 | Porreca |
| 2016/0138104 | A1 | 5/2016 | Hamamah et al. |
| 2016/0186262 | A1 | 6/2016 | Johnson |
| 2016/0201134 | A1 | 7/2016 | Liao et al. |
| 2016/0224724 | A1 | 8/2016 | Zhao et al. |
| 2016/0333416 | A1 | 11/2016 | Babiarz et al. |
| 2017/0044606 | A1 | 2/2017 | Lo et al. |
| 2018/0032671 | A1 | 2/2018 | Mazloom et al. |
| 2018/0195123 | A1 | 7/2018 | Johnson |
| 2018/0201995 | A1 | 7/2018 | Rabinowitz |
| 2018/0298439 | A1 | 10/2018 | Ryan et al. |
| 2020/0111573 | A1 | 4/2020 | Burke et al. |
| 2020/0399701 | A1 | 12/2020 | Burke et al. |
| 2020/0402610 | A1 | 12/2020 | Burke et al. |
| 2020/0402616 | A1 | 12/2020 | Burke et al. |
| 2021/0062256 | A1 | 3/2021 | Munne-Blanco et al. |
| 2022/0367063 | A1* | 11/2022 | Kumar .................. G16H 50/30 |

FOREIGN PATENT DOCUMENTS

| | | |
|---|---|---|
| WO | WO 2011/041485 | 4/2011 |
| WO | WO 2013/052557 | 4/2013 |
| WO | WO 2014/014498 | 1/2014 |
| WO | WO 2014/116881 | 7/2014 |
| WO | WO 2015/042980 A1 | 4/2015 |
| WO | WO 2017/037657 | 3/2017 |
| WO | WO 2019/051244 | 3/2019 |

OTHER PUBLICATIONS

Wilhelm et al., "Defining Transcribed Regions Using RNA-seq," Nature Protocols, Jan. 21, 2010, 5: 255-266.
Yousif et al., "The Origins and Consequences of Localized and Global Somatic Hypermutation," bioRxiv, Mar. 2018, 33 pages.
Dodds et al., "Exclusion and genomic relatedness methods for assignment of parentage using genotyping-by-sequencing data," bioRxiv, Mar. 20, 2019, 19 pages.
GenomeStudio Software, "DNA Sequencing Module Workflow," Illumina, Inc., 2009, retrieved from URL<https://www.illumina.com/Documents/products/technotes/technote_genomestudio_dna_sequencing_module_workflow.pdf>, 1 page.
GenomeStudio, "Gene Expression Module v1.0; User Guide," Illumina, 2008, retrieved from URL<https://supportillumina.com/content/dam/illumina-support/documents/documentation/software_documentation/genomestudio/genomestudio-2011-1/genomestudio-gx-module-v1-0-user-guide-11319121-a.pdf>, 186 pages.
Wikipedia, "Coverage," Jan. 9, 2023, retrieved from URL<https://en.wikipedia.org/wiki/Coverage (genetics)>, 4 pages.
Yan et al., "Live births after simultaneous avoidance of monogenic diseases and chromosome abnormality by next-generation sequencing with linkage analyses," Proceedings of the National Academy of Sciences, Dec. 29, 2015, 112(52): 15964-15969.
International Search Report and Written Opinion dated Sep. 25, 2020 issued in related PCT App. No. PCT/US2020/038815 (17 pages).
International Search Report and Written Opinion dated Sep. 15, 2020 issued in related PCT App. No. PCT/US2020/038824 (15 pages).
Marin D, et al.: "The perks of going targeted: sample contamination, DNA fingerprinting and chromosomal mosaicism accurately predicted by targeted NGS-based comprehensive chromosome screening"; Fertility and Sterility, vol. 108, No. 3, Sep. 2017 (Sep. 2017), XP085158507, ISSN: 0015-0282, DOI: 10.1016/J. FERTNSTERT.2017.07.273, the whole document.
Marin Diego et al: "Validation of a targeted next generation sequencing-based comprehensive chromosome screening platform for detection of triploidy in human blastocysts", Reproductive Biomedicine Online, Elsevier, Amsterdam, NL, vol. 36, No. 4, Jan. 2, 2018 (Jan. 2, 2018), pp. 388-395, XP085369845, ISSN: 1472-6483, DOI: 10.1016/J. RBMO.2017.12.015.
Backenroth Daniel et al: "Haploseek: a 24-hour all-in-one method for preimplantation genetic diagnosis (PGD) of monogenic disease and aneuploidy", Genetics in Medicine, Williams and Wilkins, Bal Ti More, MD, US, vol. 21, No. 6, Nov. 19, 2018 (Nov. 19, 2018), pp. 1390-1399, XP036796398, ISSN: 1098-3600, DOI: 10.1038/S41436-018-0351-7 [retrieved on Nov. 19, 2018].
Pylyp LY, Spynenko LO, Verhoglyad NV, Mishenko AO, Mykytenko DO, Zukin VD. Chromosomal abnormalities in products of conception of first-trimester miscarriages detected by conventional cytogenetic analysis: a review of 1000 cases. J Assist Reprod Genet. Feb. 2018;35(2):265-271. doi: 10.1007/s10815-017-1069-1. Epub Oct. 30, 2017. PMID: 29086320; PMCID: PMC5845039.
Rodriguez-Purata J, Lee J, Whitehouse M, Moschini RM, Knopman J, Duke M, Sandler B, Copperman A. Embryo selection versus natural selection: how do outcomes of comprehensive chromosome screening of blastocysts compare with the analysis of products of conception from early pregnancy loss (dilation and curettage) among an assisted reproductive technology population? Fertil Steril. Dec. 2015; 104(6):1460-66.e1-12. doi: 10.1016/j.fertnstert.2015.08.007. Epub Sep. 8, 2015. PMID: 26361205.
Horiuchi, I., Wakimoto, Y., Kuwata, T et al. Cytogenetic Analysis of Spontaneous Miscarriages Using Long-Term Culturing of Chorionic Villi. J. Fetal Med. 6, 1-6 (2019). https://doi.org/10.1007/s40556-018-0190-2.
Neitzel, Dana & Robinson, Kristina & Walters-Sen, Lauren & Leahey, Jocelyn & Alouf, Charlene & Faulkner, Nicole. (2019). Clinical experience following PGT analysis of >138,000 consecutive embryos using a fast-seqs NGS-based assay. Fertility and Sterility. 112. e236. 10.1016/j.fertnstert.2019.07.1363.
Sambrook et al., Molecular Cloning: A Laboratory Manual (Third ed., Cold Spring Harbor Laboratory Press, Cold Spring Harbor, N.Y. 2000.
Sims et al. (2014), "Sequencing depth and coverage: key considerations in genomic analyses" Nature Reviews Genetics 15:121-132.
Kulski (2016) "Next-Generation Sequencing—An Overview of the History, Tools and 'Omic' Applications," in Next Generation Sequencing—Advances, Applications and Challenges, J. Kulski ed., London: Intech Open, pp. 3-60.
UCSC Genome Browser on Human Feb. 2009 (GRCh37/hg19) Assembly; printed from the internet on Nov. 19, 2020, https://genome.ucsc.edu/cgi-bin/hgGateway?db=hg19.
NCBI Resources; printed from the internet on Nov. 19, 2020, https://www.ncbi.nfm.nih.gov/assembly/GCF_000001406.39.
Bowtie, An ultrafast memory-efficient short read aligner, John Hopkins University; printed from the internet on Nov. 19, 2020, http://bowtie-bio.sourceforge.net/manual.shtml.
Poplin et al.(2018) "A Universal SNP and Small-Indel Variant Caller Using Deep Neural Networks," Nature Biotech. 36:983-987.
Richards et al. (2015) Genetics in Medicine 17:405-423.
EGAS00001001710, European Genome-phenome Archive; printed from the internet on Dec. 2, 2020 https://www.ebi.ac.uk/ega/studies/EGAS00001001710.

(56) References Cited

OTHER PUBLICATIONS

IGSR: The International Genome Sample Resource; printed from the internet on Dec. 2, 2020, https://www.internationalgenome.org/.

Browning et al., "A One-Penny Imputed Genome from Next-Generation Reference Panels," (2018) Am J Hum Genet 103(3):338-348.

Browning and Browning, "Rapid and Accurate Haplotype Phasing and Missing-Data Inference for Whole-Genome Association Studies by Use of Localized Haplotype Clustering," (2007) Am J Hum Genet 81:1084-1097.

Beagle 5.1, printed from the internet on Dec. 2, 2020 http://faculty.washington.edu/browning/beagle/beagle.html#download.

Li et al. (2009) Ann Rev Genom Hum Genet 10:387-406.

Li et al. "MaCH: Using Sequence and Genotype Data to Estimate Haplotypes and Unobserved Genotypes," (2010) Genet Epidemiol 34:816-834.

MACH Tutorial—Imputation; Center for Statistical Genetics, printed from the internet on Dec. 2, 2020, http://csg.sph.umich.edu/abecasis/MACH/tour/imputation.html.

Broad Institute, [online] "Genome Analysis Toolkit," Jan. 2020, retrieved from the internet on Nov. 19, 2020, retrieved from URL <https://gatk.broadinstitute.org/>, 1 page.

Hisano et al., "Exome QTL-seq maps monogenic locus and QTLs in barley," BMC Genomics, Biomed Central Ltd, vol. 18, No. 1, Feb. 2, 2017, pp. 1-9.

Kelk et al., "Does Laser Assisted Biopsy Introduce Mosaic or Chaotic Changes to Biopsied Cells?," ASRM Abstracts, Nov. 1, 2017, vol. 108, No. 3, 1 page.

Li et al., "Burrows-Wheeler Aligner" Feb. 28, 2010, retrieved on Dec. 7, 2020, retrieved from URL <http://biobwa.sourceforge.net/>, 2 pages.

Petkaue et al., "SNVPhyl: a single nucleotide variant phylogenomics pipeline for microbial genomic epidemiology," Microbial Genomics, vol. 3, No. 6, Jun. 8, 2017, 11 pages.

Stamoulis et al., "Optimization of signal decomposition matched filtering (SDMF) for improved detection of copy-number variations", IEEE/ACM Transactions on Computational Biology and Bioinformatics, May 1, 2016, vol. 13, No. 3, pp. 584-591.

Van Iterson et al., "A Novel and Fast Normalization Method for High-Density Arrays," Statistical Applications in Genetics and Molecular Biology, Jan. 12, 2012 vol. 11, No. 4, 31 pages.

Xu et al., "Noninvasive chromosome screening of human embryos by genome sequencing of embryo culture medium for in vitro fertilization," Proceedings of the National Academy of Sciences of the United States of America, Sep. 29, 2016, vol. 113, No. 42, pp. 11907-11912.

Daughtry et al., "Single-cell sequencing of primate preimplantation embryos reveals chromosome elimination via cellular fragmentation and blastomere exclusion," Genome Res., 2019, 29(3):367-382.

Gregg et al., "Screening for Autosomal Recessive and X-linked Conditions During Pregnancy and Preconception: a Practice Resource of the American College of Medical Genetics and Genomics (ACMG)," Genetics in Medicine, 2021, 23: 1793-1806.

Rehm et al., "ACMG Clinical Laboratory Standards for Next-Generation Sequencing," Genetics in Medicine, Sep. 2013, 15(9): 15 pages.

Sun et al., "Characterizing Sensitivity and Coverage of Clinical WGS as a Diagnostic Test for Genetic Disorders," BMC Med Genomics, 2021, 14:102, 13 pages.

Vanraden et al., "Fast Imputation Using Medium or Low-Coverage Sequence Data," BMC Genetics, Jul. 14, 2015, 16(1), 12 pages.

Zhang et al., "BasePhasing: a Highly Efficient Approach for Preimplantation Genetic Haplotyping in Clinical Application of Balanced Translocation Carriers," BMC Medical Genomics, Mar. 18, 2019, 12:52, 10 pages.

Fazekas et al., "Improving sequencing quality from PCR products containing long mononucleotide repeats," Bio Techniques, 2010, 48: 277-285, 5 pages.

Patterson et al., "Deep Learning: a Practitioner's Approach," O'Reilly Media, Inc., Jul. 2017, excerpt of pp. 78-79, 107-110 and 180, 11 pages.

* cited by examiner

SYSTEMS AND METHODS FOR DETERMINING PATTERN OF INHERITANCE IN EMBRYOS

CROSS-REFERENCE TO RELATED APPLICATIONS

This application claims the benefit of priority to U.S. Provisional Patent Application 62/865,130 filed Jun. 21, 2019, which is incorporated herein by reference in its entirety.

INCORPORATION BY REFERENCE

The disclosures of any patents, patent applications and publications cited herein are incorporated herein by reference in their entirety.

FIELD

The embodiments provided herein are generally related to systems and methods for analysis of genomic nucleic acids (e.g., genomic DNA) and classification of genomic features. Included among embodiments provided herein are systems and methods relating to determining patterns of inheritance of genomic features, such as, for example, chromosomal abnormalities, in cells, e.g., an embryo, or organisms.

BACKGROUND

In vitro fertilization (IVF) is an assisted reproductive technology that has become increasingly popular for women of advanced maternal age, couples with difficulties conceiving and as a means for facilitating gestational surrogacy. The process of fertilization involves extracting eggs, retrieving a sperm sample, and then manually combining an egg and sperm in a laboratory setting. The embryo(s) is then implanted in the host uterus to carry the embryo to term.

IVF procedures are expensive and can exact a significant emotional/physical toll on patients, so genetic screening of embryos prior to implantation is becoming increasingly common for patients undergoing an IVF procedure. For example, currently IVF embryos are commonly screened for genetic abnormalities (e.g., SNP, aneuploidy, etc.) and other conditions that can affect viability of transfer (i.e., embryo implantation viability).

Upon identification of an abnormality, e.g., an aneuploidy, it is often desirable to also determine the pattern of inheritance (POI) of the abnormality as being from the mother or the father. However, this currently requires expensive additional procedures using microarrays or other types of higher coverage genomic sequencing.

As such, there is a need for more rapid, less costly systems and methods to classify the origin of chromosomal abnormalities, e.g., aneuploidies, as being from maternal or paternal lineage, to determine the pattern of inheritance of an abnormality.

SUMMARY

Provided herein are methods and systems for analysis of genomic nucleic acids (genomic DNA) and classification of genomic features, including, for example, genetic abnormalities. In some embodiments, the methods and systems are used in detecting or identifying a genomic feature and/or determining the pattern of inheritance of a genomic feature, such as, for example, classifying the parental origin of a genomic feature of genomic nucleic acids (genomic DNA) in cells, e.g., diploid cells or an embryo, and/or organisms. In some embodiments, the genomic feature is a genetic abnormality, for example, a chromosomal abnormality such as an aneuploidy, polyploidy and/or segmental chromosome gains/losses.

Methods and systems provided herein include methods of analyzing, assessing, characterizing and/or determining genomes, genomic features and/or genomic nucleic acid (genomic DNA) sequences of a cell or organism. In some embodiments, genomic sequence data used in the methods and systems provided herein are obtained, for example, by nucleic acid sequencing methods, e.g., next generation sequencing (NGS) methods, such as low-coverage and/or low-depth (e.g., low-resolution) whole genome sequencing methods. The ability to utilize lower resolution nucleic acid sequencing data obtained from low-coverage and/or low-depth (e.g., low-resolution) whole genome sequencing in methods and systems provided herein provides significant advantages, including, for example, increased efficiency (e.g., allowing multiplex sequencing of a large number of samples) and reduced time and costs. In some embodiments, methods and systems provided herein are used in detecting and/or identifying one or more, or a plurality, of genomic features and/or assessing, classifying or determining a pattern of inheritance of one or more, or a plurality, of genomic features to determine, predict and/or infer the parental origin or lineage of the genomic feature as being maternal or paternal. In some embodiments, the genomic feature is a genetic abnormality, such as, for example, a chromosomal abnormality. In some embodiments, the genomic feature is a chromosomal abnormality, such as, for example, aneuploidy and/or polyploidy. In some embodiments, the methods and systems are used to detect, identify and/or classify the parental origin of one or more, or a plurality of, genomic features in embryos, including, for example, embryos generated through IVF, prior to implantation. In some embodiments, methods and systems provided herein are used to detect, identify and/or classify the parental origin of a chromosomal abnormality, such as aneuploidy and/or polyploidy, in an embryo, such as an IVF embryo, prior to implantation. In some embodiments, methods and systems provided herein include detecting, identifying and/or analyzing single nucleotide variation (SNV) in the genome of a cell(s), e.g., an embryo, and organisms. In some of such embodiments, the SNV data includes or consists of low resolution sequence information obtained from low-coverage and/or low-depth (e.g., low-resolution) whole genome sequencing in methods. In some embodiments, the systems and methods are optimized for using SNV data, such as SNV data generated from low-coverage and/or low-depth (e.g., low-resolution) whole genome sequencing methods, to detect, identify and/or classify the parental origin or lineage of a chromosomal abnormality, such as aneuploidy, segmental chromosome gains/losses and/or polyploidy, in a cell(s), e.g., an embryo, or organism.

In accordance with various embodiments, a method is provided for determining pattern of inheritance in an embryo for a region of interest. The method can comprise receiving embryo, maternal and paternal sequence data, wherein the maternal sequence data is from a mother of the embryo and the paternal sequence data is from a father of the embryo. The method can comprise aligning the received sequence data to a reference genome, identifying a region of interest in the aligned embryo sequence data, and identifying single nucleotide polymorphisms (SNPs) in the maternal sequence data, paternal sequence data, and the identified region of interest in the embryo sequence data. The method can comprise imputing missing gaps in the maternal sequence data and the paternal sequence data using an imputation reference. The method can comprise counting the number of SNPs that are common between the embryo and the mother in the identified region of interest for the embryo sequence data and a corresponding region on the maternal sequence data to determine a maternal contribution value. The method can comprise counting the number of SNPs that are common between the embryo and the father in the identified region of interest for the embryo sequence data and a corresponding region on the paternal sequence data to determine a paternal contribution value. The method can comprise classifying a pattern of inheritance for the embryo as maternal or paternal based on the relative contribution values between mother and father.

In accordance with various embodiments, a non-transitory computer-readable medium storing computer instructions is provided for determining pattern of inheritance in an embryo for a region of interest. The method can comprise receiving embryo, maternal and paternal sequence data, wherein the maternal sequence data is from a mother of the embryo and the paternal sequence data is from a father of the embryo. The method can comprise aligning the received sequence data to a reference genome, identifying a region of interest in the aligned embryo sequence data, and identifying single nucleotide polymorphisms (SNPs) in the maternal sequence data, paternal sequence data, and the identified region of interest in the embryo sequence data. The method can comprise imputing missing gaps in the maternal sequence data and the paternal sequence data using an imputation reference. The method can comprise counting the number of SNPs that are common between the embryo and the mother in the identified region of interest for the embryo sequence data and a corresponding region on the maternal sequence data to determine a maternal contribution value. The method can comprise counting the number of SNPs that are common between the embryo and the father in the identified region of interest for the embryo sequence data and a corresponding region on the paternal sequence data to determine a paternal contribution value. The method can comprise classifying a pattern of inheritance for the embryo as maternal or paternal based on the relative contribution values between mother and father.

In accordance with various embodiments, a system is provided for determining pattern of inheritance in an embryo for a region of interest. The system can comprise a data store for receiving embryo, maternal and paternal sequence data, wherein the maternal sequence data is from a mother of the embryo and the paternal sequence data is from a father of the embryo. The system can comprise a computing device communicatively connected to the data store, the computing device comprising an ROI engine configured to align the received sequence data to a reference genome and identify a region of interest in the aligned embryo sequence data. The computing device can comprise a SNP identification engine configure to identify single nucleotide polymorphisms (SNPs) in the maternal sequence data, paternal sequence data, and the identified region of interest in the embryo sequence data. The computing device can comprise an imputation engine configured to impute missing gaps in the maternal sequence data and the paternal sequence data using an imputation reference. The computing device can comprise a POI engine. The POI engine can be configured to count the number of SNPs that are common between the embryo and the mother in the identified region of interest for the embryo sequence data and a corresponding region on the maternal sequence data to determine a maternal contribution value, count the number of SNPs that are common between the embryo and the father in the identified region of interest for the embryo sequence data and a corresponding region on the paternal sequence data to determine a paternal contribution value, and classify a pattern of inheritance for the embryo as maternal or paternal based on the relative contribution values between mother and father. The system can further comprise a display communicatively connected to the computing device and configured to display a report containing the classified pattern of inheritance for the embryo.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 5A shows a graph of the number of embryo variant alleles shared with paternal source (OvP) vs. the number of embryo variant alleles shared with maternal source (OvM) for each of the 23 chromosomes (blue dots), in accordance with various embodiments. The dotted diagonal line represents the points on the graph at which the number of embryo variant alleles shared with the maternal source would be equal to the number of embryo variant alleles shared with the paternal source for each chromosome. FIG. 5B is another graphic presentation of the results shown in FIG. 5A showing the ratio of counts of shared alleles with mother to counts of shared alleles with father per chromosome, in accordance with various embodiments.

Figure 1:
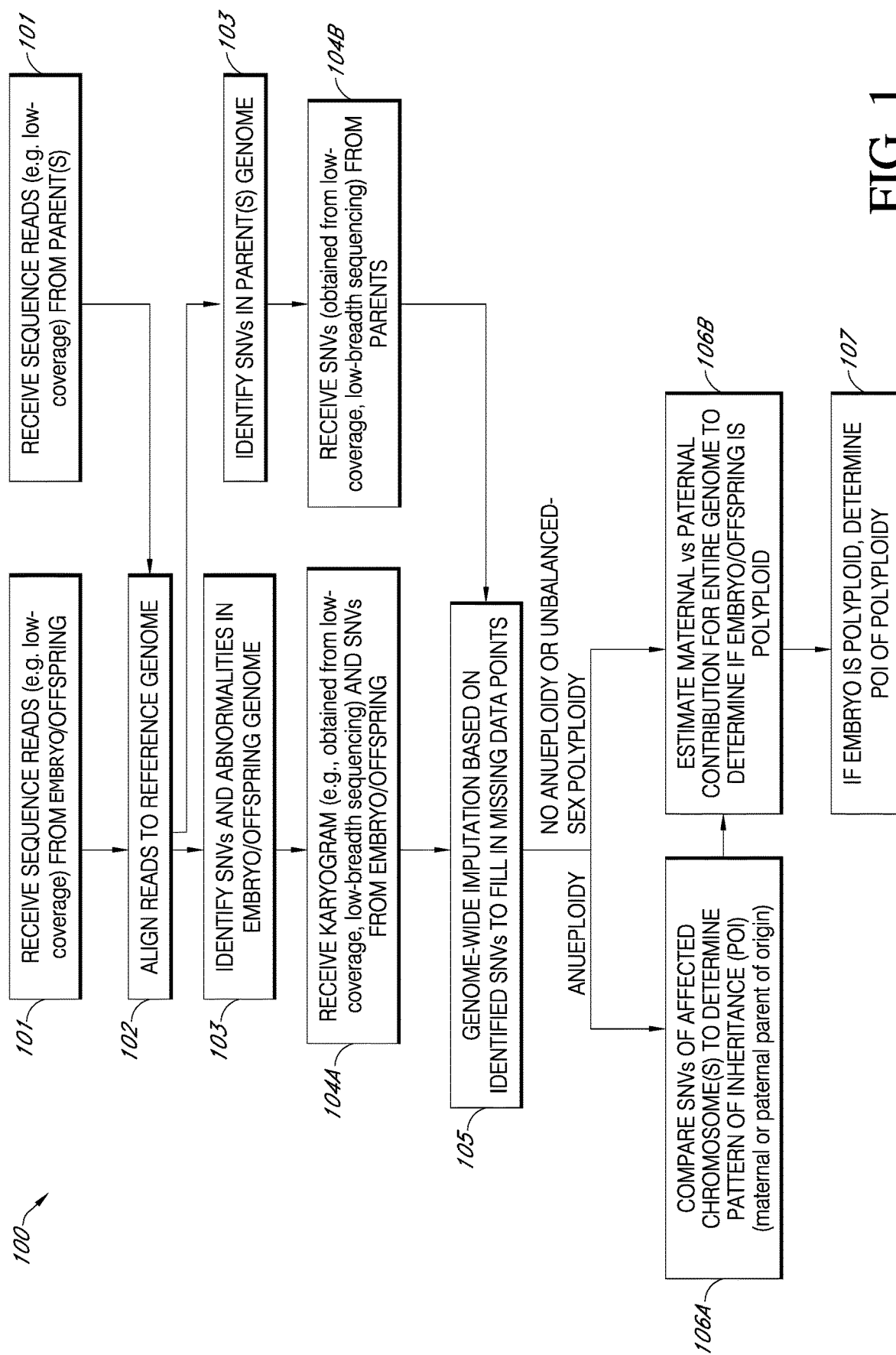
FIG. 1 is an exemplary flowchart showing a method for determining or classifying pattern of inheritance (POI) of a genetic abnormality as being or maternal or paternal origin, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

The above-identified figures are provided by way of representation and not limitation. The figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

DETAILED DESCRIPTION

Provided herein are methods and systems for analysis of genomic nucleic acids (genomic DNA) and classification of genomic features, including, for example, genetic abnormalities. In some embodiments, the methods and systems are used in the determining the pattern of inheritance of a genomic feature, such as, for example, classifying the parental origin of a genomic feature of nucleic acids in cells, e.g., diploid cells or an embryo, and organisms.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. Standard molecular biological techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and standard techniques described herein are those well-known and commonly used in the art.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

DNA (deoxyribonucleic acid) is a chain of nucleotides containing 4 types of nucleotides; A (adenine), T (thymine), C (cytosine), and G (guanine), and RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

As used herein, the term "cell" is used interchangeably with the term "biological cell." Non-limiting examples of biological cells include eukaryotic cells, plant cells, animal cells, such as mammalian cells, reptilian cells, avian cells, fish cells or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells and the like. A mammalian cell can be, for example, from a human, mouse, rat, horse, goat, sheep, cow, primate or the like.

A genome is the genetic material of a cell or organism, including animals, such as mammals, e.g., humans, and comprises nucleic acids, i.e., genomic DNA. In humans, total DNA includes, for example, genes, noncoding DNA and mitochondrial DNA. The human genome typically contains 23 pairs of linear chromosomes: 22 pairs of autosomal chromosomes (autosomes) plus the sex-determining X and Y chromosomes. The 23 pairs of chromosomes include one copy from each parent. The DNA that makes up the chromosomes is referred to as chromosomal DNA and is present in the nucleus of human cells (nuclear DNA). Mitochondrial DNA is located in mitochondria as a circular chromosome, is inherited from only the female parent, and is often referred to as the mitochondrial genome as compared to the nuclear genome of DNA located in the nucleus.

As used herein, the phrase "genomic feature" refers to a defined or specified genome element or region. In some instances, the genome element or region can have some annotated structure and/or function (e.g., a chromosome, a gene, protein coding sequence, mRNA, tRNA, rRNA, repeat sequence, inverted repeat, miRNA, siRNA, etc.) or be a genetic/genomic variant (e.g., single nucleotide polymorphism/variant, insertion/deletion sequence, copy number variation, inversion, etc.) which denotes one or more nucleotides, genome regions, genes or a grouping of genome regions or genes (in DNA or RNA) that have undergone changes as referenced against a particular species or subpopulations within a particular species due to, for example, mutations, recombination/crossover or genetic drift.

Ploidy refers to the number of sets (designated as n) of homologous chromosomes in the genome of a cell or organism. For example, a cell or organism having one set of chromosomes is referred to as monoploid. A cell or organism having two sets of homologous chromosomes (2n) is referred to as diploid. Polyploidy is the condition in which cells, e.g., an embryo, or organisms possess more than two complete haploid sets of chromosomes. Haploid refers to cells that have half of the usual complete set of somatic cell chromosomes of an organism. For example, gametes, or reproductive (sex) cells, such as ova and sperm cells in humans, are haploid. Fusion of haploid gametes during fertilization yields a diploid zygote containing one set of homologous chromosomes from the female gamete and one set of homologous chromosomes from the male gamete. A human embryo with a normal number of autosomes (22) and a single sex chromosome pair (XX or XY) is referred to as a euploid embryo. Thus, for humans, the euploid condition is diploid. In various embodiments, the phrase "all chromosomes" can include all autosomes and sex chromosomes. In various embodiments, the phrase "all chromosomes" does not include sex chromosomes.

The term "allele" refers to alternative forms of a gene. In humans or other diploid organisms, there are two alleles at each genetic locus. Alleles are inherited from each parent: one allele is inherited from the mother and one allele is inherited from the father. A pair of alleles represents the genotype of a gene. If the two alleles at a particular locus are identical, the genotype is referred to as homozygous. If there are differences in the two alleles at a particular locus, the genotype is referred to as heterozygous.

The term "haplotype" refers to a set, or combination, of variations, or polymorphisms, in a chromosome that tend to co-segregate due to proximity in the chromosome. Haplotypes can be described with respect to combinations of variations in a single gene, multiple genes or in sequences between genes. Because of the closeness of the variations in a haplotype, there tends to be little to no recombination or crossover of the locations in which the variations occur and they tend to pass through generations and be inherited together.

As used herein, the phrase "genetic abnormality" refers to a change in a genome relative to a normal, wild-type or reference genome. Generally, genetic abnormalities include chromosomal abnormalities and gene defects. Typically, gene defects include alterations including, but not limited to, single base mutations, substitutions, insertions and deletions and copy number variations. Chromosomal abnormalities include alterations in chromosome number or structure, e.g., duplication and deletion, such as a repeat or loss of a region of a chromosome, inversion and translocation. A common chromosomal abnormality is referred to as aneuploidy which is an abnormal chromosome number due to an extra or missing chromosome. For example, monosomy in a human is an abnormality characterized by a chromosome with a copy loss (only one copy instead of the normal two copies). Trisomy in a human is an abnormality characterized by a chromosome copy gain (three copies instead of the normal two copies). An embryo with an abnormal number of chromosomes is referred to as an aneuploid embryo. Most aneuploidies are of maternal origin and result from errors in segregation during oocyte meiosis. Thus, meiotic aneuploidies will occur in all cells of an embryo. However, mitotic errors are also common in human preimplantation embryos and can result in mitotic aneuploidies and chromosomally mosaic embryos having multiple populations of cells (e.g., some cells being aneuploid and some being euploid). Polyploidy in a human cell is an abnormality in which the cell, e.g., in an embryo, possesses more than two complete sets of chromosomes. Examples of polyploidy include triploidy (3n) and tetraploidy (4n). Polyploidy in humans can occur in several forms that result in having either balanced sex chromosomes or unbalanced sex chromosomes (e.g., detectable by CNV methods). A balanced-sex polyploidy in humans contains 3 or more complete copies of the haploid genome in which each copy contains only X chromosomes (e.g., 69:XXX or 92:XXXX) or contains an equivalent number of X and Y chromosomes (e.g., 92:XXYY). An unbalanced-sex polyploidy in humans contains 3 or more complete copies of the haploid genome in which at least one copy contains a Y chromosome (e.g., 69:XXY, 69:XYY) and does not contain an equivalent copy number of X and Y chromosomes. Chromosomal abnormalities can have a number of different effects on cells and organisms, including molar pregnancies, miscarriages and genetic disorders and diseases.

In general, genomic variants can be identified using a variety of techniques, including, but not limited to: array-based methods (e.g., DNA microarrays, etc.), real-time/digital/quantitative PCR instrument methods and whole or targeted nucleic acid sequencing systems (e.g., NGS systems, capillary electrophoresis systems, etc.). With nucleic acid sequencing, resolution or coverage can be at one or more levels and is some cases is available at single base resolution.

As used herein, the phrase "pattern of inheritance" refers to the manner and dosage of transmission of a genomic feature, such as, for example, aneuploidy, in the genome of a cell(s), offspring, e.g., an embryo or organism from parent cells or organisms such as diploid cells and organisms. For example, in humans, the offspring, e.g., embryo, receives one gene allele from each parent (one maternal and one paternal) which then make up the two alleles in the diploid cells of the offspring. A pattern of inheritance of a particular allele or genomic feature in an offspring, e.g., an embryo, defines which parent transmitted the genomic feature to the offspring. The parent from whom the genomic feature was transmitted to the offspring or embryo is referred to as the parent of origin. Inheritance can be balanced (expected; equal contribution from each parent) or imbalanced (insufficient or excess). For example, for an embryo possessing Trisomy 21 in which one copy of chromosome 21 was inherited paternally and two copies were inherited maternally, it is said that the parent of origin of aneuploid is maternal. Conversely, for Monsomoy 18, in which an embryo inherited a maternal copy and no paternal copy of chromosome 18, it can be said that the parent of origin for that feature is paternal.

As used herein, "offspring" refers to the product of the union of gametes (e.g., female and male germ cells) and includes, but is not limited to, e.g., a blastomere, a zygote, an embryo, fetus, neonate or child. Offspring DNA can be obtained from any source, including, for example, a blastomere biopsy, a trophectoderm biopsy, an inner cell mass biopsy, a blastocoel biopsy, embryo spent media, cfDNA, products of conception, chorionic villus samples and/or amniocentesis.

As used herein, "parent" or "genetic parent" refers to a contributor of a gamete to an offspring and includes, for example, egg and sperm donors so long as the gamete DNA originates from the donor.

The phrase "mosaic embryo" denotes embryos containing two or more cytogenetically distinct cell lines. For example, a mosaic embryo can contain cell lines with different types of aneuploidy or a mixture of euploid and genetically abnormal cells containing DNA with genetic variants that may be deleterious to the viability of the embryo during pregnancy.

The phrase "next generation sequencing" (NGS) refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the MISEQ, HISEQ and NEXTSEQ Systems of Illumina and the Personal Genome Machine (PGM), Ion Torrent, and SOLiD Sequencing System of Life Technologies Corp, provide massively parallel sequencing of whole or targeted genomes. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing process performed to determine some information relating to at least one biomolecule (e.g., nucleic acid molecule).

The term "read" with reference to nucleic acid sequencing refers to the sequence of nucleotides determined for a nucleic acid fragment that has been subjected to sequencing, such as, for example, NGS. Reads can be any a sequence of any number of nucleotides which defines the read length.

The phrase "sequencing coverage" or "sequence coverage," used interchangeably herein, generally refers to the relation between sequence reads and a reference, such as, for example, the whole genome of cells or organisms, one locus in a genome or one nucleotide position in the genome. Coverage can be described in several forms (see, e.g., Sims et al. (2014) Nature Reviews Genetics 15:121-132). For example, coverage can refer to how much of the genome is being sequenced at the base pair level and can be calculated as $NL/G$ in which N is the number of reads, L is the average read length, and G is the length, or number of bases, of the genome (the reference). For example, if a reference genome is 1000 Mbp and 100 million reads of an average length of 100 bp are sequenced, the redundancy of coverage would be 10×. Such coverage can be expressed as a "fold" such as 1×, 2×, 3×, etc. (or 1, 2, 3, etc. times coverage). Coverage can also refer to the redundancy of sequencing relative to a reference nucleic acid to describe how often a reference sequence is covered by reads, e.g., the number of times a single base at any given locus is read during sequencing. Thus, there may be some bases which are not covered and have a depth of 0 and some bases that are covered and have a depth of anywhere between, for example, 1 and 50. Redundancy of coverage provides an indication of the reliability of the sequence data and is also referred to as coverage depth. Redundancy of coverage can be described with respect to "raw" reads that have not been aligned to a reference or to aligned (e.g., mapped) reads. Coverage can also be considered in terms of the percentage of a reference (e.g., a genome) covered by reads. For example, if a reference genome is 10 Mbp and the sequence read data maps to 8 Mbp of the reference, the percentage of coverage would be 80%. Sequence coverage can also be described in terms of breadth of coverage which refers to the percentage of bases of a reference that are sequenced a given number of times at a certain depth.

As used herein, the phrase "low coverage" with respect to nucleic acid sequencing refers to sequencing coverage of less than about 10×, or about 0.001× to about 10×, or about 0.002× to about 0.2×, or about 0.01× to about 0.05×.

As used herein, the phrase "low depth" with respect to nucleic acid sequencing refers to an average genome-wide sequencing depth of less than about 20× or less than about 10×, or about 0.1× to about 10×, or about 0.2× to about 5×, or about 0.5× to about 2×.

The term "resolution" with reference to genomic sequence nucleic acid sequence refers to the quality, or accuracy, and extent of the genomic nucleic acid sequence (e.g., DNA sequence of the entire genome or a particular region or locus of the genome) obtained through nucleic acid sequencing of a cell(s), e.g., an embryo, or organism. The resolution of genomic nucleic DNA sequence is primarily determined by the coverage and depth of the sequencing process and involves consideration of the number of unique bases that are read during sequencing and the number of times any one base is read during sequencing. The phrases "low resolution sequence" or "low resolution sequence data" or "sparse sequence data," which are used interchangeably herein, with reference to genomic nucleic acid sequence (genomic DNA) of a cell(s), e.g., an embryo, offspring or organism, refer to the nucleotide base sequence information of genomic nucleic acid (genomic DNA) that is obtained through low-coverage and low-depth sequencing methods.

Nucleic Acid (DNA) Sequence Data Generation

Some embodiments of the methods and systems provided herein for the analysis of genomic nucleic acids (genomic DNA) and classification of genomic features include analysis of nucleotide sequences of the genome of cells and/or organisms. In some embodiments, the methods and systems provided herein include analysis of sequences obtained from whole genome sequencing of a cell(s) and/or organism(s). In some embodiments, the methods and systems provided herein include analysis of sequences of the whole genome of a cell(s) and/or organism(s). Nucleic acid sequence data can be obtained using a variety of methods described herein and/or know in the art. In one example, sequences of genomic nucleic acid (genomic DNA) of cells, for example cells of an embryo, may be obtained from next-generation sequencing (NGS) of DNA samples extracted from the cells. NGS, also known as second-generation sequencing, is based on high-throughput, massively parallel sequencing technologies that involve sequencing of millions of nucleotides generated by nucleic acid amplification of samples of DNA (e.g., extracted from embryos) in parallel (see, e.g., Kulski (2016) "Next-Generation Sequencing—An Overview of the History, Tools and 'Omic' Applications," in Next Generation Sequencing—Advances, Applications and Challenges, J. Kulski ed., London: Intech Open, pages 3-60).

Nucleic acid samples to be sequenced by NGS are obtained in a variety of ways, depending on the source of the sample. For example, human nucleic acids may readily be obtained via cheek brush swabs to collect cells from which nucleic acids are then extracted. In order to obtain optimum amounts of DNA for sequencing from embryos (for example, for pre-implantation genetic screening), cells (e.g., 5-7 cells) commonly are collected through trophectoderm biopsy during the blastocyst stage. Fetal DNA can be obtained, for example, from products or conception, chorionic villus samples and/or amniocentesis. DNA samples require processing, including, for example, fragmentation, amplification and adapter ligation prior to sequencing via NGS. Manipulations of the nucleic acids in such processing may introduce artifacts (e.g., GC bias associated with polymerase chain reaction (PCR) amplification), into the amplified sequences and limit the size of sequence reads. NGS methods and systems are thus associated with error rates that may differ between systems. Additionally, software used in conjunction with identifying bases in a sequence read (e.g., base-calling) can affect the accuracy of sequence data from NGS sequencing. Such artifacts and limitations can make it difficult to sequence and map long repetitive regions of a genome and identify polymorphic alleles and aneuploidy in genomes. For example, because about 40% of the human genome is comprised of repeat DNA elements, shorter single reads of identical sequence that align to a repeat element in a reference genome often cannot be accurately mapped to a particular region of the genome. One way to address and possibly reduce some of the effects of errors and/or incompleteness in sequence determination is by increasing sequencing coverage and/or depth. However, increases in sequencing coverage are associated with increased sequencing times and costs. Paired-end sequencing can also be utilized, which increases accuracy in placement of sequence reads, e.g., in long repetitive regions, when mapping sequences to a genome or reference, and increases resolution of structural rearrangements such as gene deletions, insertions and inversions. For example, in some embodiments of methods provided herein, use of data obtained from paired-end NGS of DNA from embryos increased read mapping by an average of 15%. Paired-end sequencing methods are known in the art and/or described herein and involve determining the sequence of a nucleic acid fragment in both directions (i.e., one read from one end of the fragment and a second read from the opposite end of the fragment). Paired-end sequencing also effectively increases sequencing coverage redundancy by doubling the number of reads and particularly increases coverage in difficult genomic regions.

Three main types of nucleic acid NGS sequencing are commonly performed: whole genome sequencing (WGS), whole exome sequencing (WES) and targeted sequencing (TS). Whole genome sequencing is a comprehensive method in which the entire genome, as opposed to a portion thereof, is sequenced. WES is sequencing of the protein-coding regions (exons) of the genome which accounts for only about less than 2% of the genome. Targeted sequencing is a high-depth coverage type of sequencing in which a one or a limited number of specific regions of the genome are sequenced. Targeted sequencing is typically performed using amplicon-based enrichment, in which specific primers are used to amplify only particular regions of interest (targeted amplification) from which nucleic acid libraries are prepared for sequencing or capture-based methods in which fragmented nucleic acids are hybridized to capture oligonucleotides to isolate regions of interest for sequencing.

Nucleic Acid (DNA) Sequence Analysis

In some embodiments of the methods and systems provided herein for the analysis of genomic nucleic acids (genomic DNA) and classification of genomic features, the sequences of DNA obtained from cells, e.g., embryo cells, or organisms are used to reconstruct the genome (or portions of it) of the cells/organisms using methods of genomic mapping. Typically, genomic mapping involves matching sequences to a reference genome (e.g., a human genome) in a process referred to as alignment. Examples of human reference genomes that may be used in mapping processes include releases from the Genome Reference Consortium such as GRCh37 (hg19) released in 2009 and GRCh38 (hg38) released in 2013. Through alignment, sequence reads are assigned to genomic loci typically using computer programs to carry out the matching of sequences. Numerous alignment programs are publicly available and include Bowtie and BWA. Sequences that have been processed (for example to remove PCR duplicates and low-quality sequences) and matched to a locus are often referred to as aligned and/or mapped sequences or aligned and/or mapped reads.

In mapping of sequence reads to a genomic reference, it is possible to detect and/or identify single nucleotide variants (SNV). Single nucleotide variants are the result of variation in the genome at a single nucleotide position. Several different NGS analysis programs for SNV detection (e.g., variant calling software) are publicly available, known in the art and/or described herein (e.g., including but not limited to GATK (see, e.g., https://gatk.broadinstitute.org/) and deepvariant (see, e.g., Poplin et al (2018) Nature Biotech. 36:983-987). After alignment, the bcftools software (open source) is used to generate a pileup of all bases identified with a minimum coverage (e.g., 1) and minimum depth (e.g., 1) and generate a genotype call from the bam file generated during alignment. Detection and identification of genomic features, such as chromosomal abnormalities, e.g., aneuploidies, through genome mapping of sequences from sample nucleic acids (DNA) of cells or organisms presents particular challenges, particularly when sequence data is obtained from low-coverage and/or low resolution sequencing methods. The major challenges in this approach are derived from the concept that NGS methods are prone to introducing errors into the sequencing read during read generation. With error rates anywhere between 1:100 and 1:10,000, depending on the sequencing platform methodology, identifying the difference between a variant and sequencing error at low-coverage and/or low-depth sequencing provides a unique and difficult informatics challenge. Computer programs and systems are known in the art and/or described herein for increasing the ease and/or accuracy of interpretation of sequence data in identifying certain genomic features. For example, systems and methods for automated detection of chromosomal abnormalities including segmental duplications/deletions, mosaic features, aneuploidy and polyploidy with unbalanced sex chromosomes are described in U.S. Patent Application Publication No. 2020/0111573 which is incorporated in its entirety by reference herein. Such methods include de-noising/normalization (to de-noise raw sequence reads and normalize genomic sequence information to correct for locus effects) and machine learning and artificial intelligence to interpret (or decode) locus scores into karyograms. For example, after sequencing is completed, the raw sequence data is demultiplexed (attributed to a given sample), reads are aligned to a reference genome such as, e.g., HG19, and the total number of reads in each 1-million base pair bin is counted. This data is normalized based on GC content and depth and tested against a baseline generated from samples of known outcome. Statistical deviations from a copy number of 2 are then reported (if present, if not=euploid) as aneuploidy. Using this method, meiotic aneuploidy and mitotic aneuploidy can be distinguished from each other based on the CNV metric. Based on the deviations from normal, a karyotype is generated with the total number of chromosomes present, any aneuploidies present, and the mosaic level (if applicable) of those aneuploidies.

Artifacts, variations in coverage and errors that can occur in NGS also present challenges in use of sequence data to accurately classify particular genomic features, such as in assessing the pattern of inheritance of a genomic feature and determining or predicting/inferring parental origin of a genomic feature. For example, challenges of using low-coverage and/or low-depth (e.g., low-resolution) sequence data that can arise in analysis of the pattern of inheritance of a genomic feature, e.g., aneuploidy, include obtaining an extremely low number-to-no high-quality, high-depth SNPs that would meet the standard American College of Medical Genetics requirements (see, e.g., Richards et al. (2015) Genetics in Medicine 17:405-423) for accurate calling leading to a lack of overlap in the sequences of offspring (e.g., an embryo) and parent(s) (e.g, mother and/or father) and preventing accurate assessment of phasing/haplotype determination. Increasing sequence coverage, although with its associated decreases in efficiency and increases in cost, may improve NGS sequence data such that it can be used in determining patterns of inheritance of a genomic feature. Other methods for meeting the challenges associated with assessing pattern of inheritance to determine parental origin of a genomic feature, e.g., aneuploidy, include use of microarrays and fluorescence in situ hybridization (FISH) which are not high-throughput technologies as is NGS and are also more costly and require longer times to carry out analyses.

Provided herein are improved, efficient, rapid, and cost-effective methods and systems for detecting and/or identifying one or more, or a plurality, of genomic features of a cell(s), e.g., cells of an embryo, offspring or an organism(s) and/or assessing, classifying or determining a pattern of inheritance of one or more, or a plurality, of genomic features to determine, predict and/or infer the parental origin or lineage of the genomic feature as being maternal or paternal. In some embodiments of methods provided herein, relatively low-coverage and/or low-depth (e.g., low-resolution) sequence data are used to identify genomic features, such as, for example, chromosomal abnormalities, of cells, e.g., cells of an embryo, offspring or organism and/or assess the pattern of inheritance of the genomic feature to determine, predict and/or infer the parental origin of the genomic feature as being maternal or paternal. In some embodiments, the methods, and systems incorporating the methods, use DNA sequence data (e.g., low-resolution sequence data) obtained from low-coverage and/or low-breadth whole genome sequencing of DNA samples of the total genomic nucleic acids (genomic DNA) or total DNA (or total nuclear DNA) of a cell(s) as opposed to being obtained from sequencing of only a portion or pre-determined specific targeted regions of a genome. In some embodiments, the methods and systems are used to classify the pattern of inheritance of genomic features in embryos, including, for example, embryos generated through IVF, prior to implantation. In some embodiments, methods and systems provided herein are used to classify the pattern of inheritance of a chromosomal abnormality, such as aneuploidy, polyploidy and/or chromosomal segmental gains and/or losses (e.g., segmental gains and/or losses of about 20 megabases or greater in size), in an embryo, such as an IVF embryo, prior to implantation.

FIG. 1 is a diagrammatic representation of the workflow 100 of an exemplary method for detecting and/or identifying a genomic feature and/or assessing, classifying, determining, predicting and/or inferring patterns of inheritance and/or parental origin of one or more genomic features of genomic nucleic acids (genomic DNA) of a cell(s), e.g., an embryo, or an organism(s). In some embodiments, the method is used to detect or identify a chromosomal abnormality (e.g., polyploidy, such as balanced-sex chromosome polyploidy) and/or assess, classify, determine, predict and/or infer patterns of inheritance and/or parental origin of one or more chromosomal abnormalities. In some embodiments, the chromosomal abnormality is aneuploidy, such as, e.g., meiotic aneuploidy, and/or polyploidy (e.g., balanced-sex chromosome polyploidy). As shown in steps 101 and 102 of FIG. 1, sequence reads (data) from sequencing of DNA of an offspring, e.g., embryo, and the assumed maternal and paternal contributors (mother and father, or parents) are received and aligned to a reference (e.g., human) genome, using any suitable alignment software program with the proper settings, for mapping. In some embodiments of the method 100, the sequence reads are obtained from low-coverage and/or low-depth (e.g., low-resolution) sequencing of offspring and parent genomic nucleic acids (genomic DNA), e.g., low-coverage and/or low-depth (e.g., resolution) whole genome sequencing of the DNA. In step 103, the sequence data are analyzed a to detect and/or identify SNVs and chromosomal abnormalities, such as chromosomal copy number variation (CNV) and structural copy number variations (e.g., aneuploidy, unbalanced-sex polyploidy and segmental chromosome gains and losses), of the offspring and to detect and/or identify SNVs of the parents. The analysis in step 103 for detection/identification of chromosomal abnormalities is referred to as "CNV" analysis herein. A karyogram containing the final copy number analysis result is generated for the offspring and it, and the SNV data files for the offspring and parents are received in step 104A and 104B. In some embodiments, the method begins at step 104A and 104B with receiving of a karyogram and SNV data for the offspring and SNV data for the parents which can be based on nucleic acid sequence information obtained through low-coverage and/or low-depth (e.g., low-resolution) sequencing of offspring and parent genomic nucleic acids (genomic DNA), e.g., low-coverage and/or low-depth (e.g., resolution) whole genome sequencing of the DNA. In some instances, the sequence reads used in generating the karyogram and SNV data are obtained through low-coverage and/or low-depth (e.g., low-resolution) paired-end sequencing methods which can provide a magnitude of order increase in data. Methods for analysis and interpretation of mapped reads are known in the art and/or described herein. For example, in some embodiments, the karyogram and SNV data are generated in a process that includes analysis of mapped reads conducted as described in U.S. Patent Application Publication No. 2020/011573. For example, using artificial intelligence (AI)/machine learning (ML), copy number variations in a de-noised sample genomic sequence dataset may be identified when a frequency of genomic sequence reads aligned to a chromosomal position deviates from a frequency threshold. The karyotype of the embryo is then determined from this analysis The single nucleotide variants (SNVs) identified in the DNA from the offspring and both gamete contributors (genetic parents) in this exemplary method are used in predicting or inferring alleles and/or haplotypes in the embryo and parents. If more than 1% of a population does not carry the same nucleotide at a specific position in the genome, the SNV is often referred to as a single nucleotide polymorphism (SNP). An SNV is typically a more generic term for less well-characterized loci. There are about 10 million or more SNPs located throughout the human genome, on average every 200 bp. Although some SNPs may be associated with traits or disorders, most have no known function. No two individuals (except identical twins) have the same pattern of SNPs which exist as major and minor isoforms within a given population. SNV and SNP are used interchangeably herein. In one embodiment of the methods and systems provided herein for detecting and/or identifying a genomic feature (e.g., polyploidy, such as balanced-sex chromosome polyploidy) and/or assessing, classifying, determining, predicting and/or inferring patterns of inheritance and/or parental origin of one or more genomic features (e.g., aneuploidy and/or polyploidy), genotype imputation (step 105 of FIG. 1) is used to construct and infer predicted alleles and/or haplotypes for all chromosomes of the genome of an offspring (e.g., embryo) and its respective gamete contributors or genetic parents based on analysis of the SNV identified in sequences of the genomes.

Low-coverage and/or low-depth (e.g., low resolution) sequencing yields sparse data with missing datapoints and thus provides a probabilistic representation of genotypes (genotype likelihoods). Genotype imputation methods are used to refine genotype likelihoods and fill in gaps due to sparsely mapped sequence reads resulting from low-coverage and/or low-depth (e.g., low-resolution) sequencing of offspring and parent genomic nucleic acids (genomic DNA) where the amount of overlap of sequence information between the embryo and parents may be limited. Imputation is a statistical inference of missing genotypes and haplotypic phase whereby alleles or haplotypes can be inferred for all chromosomes of the genome of an offspring (e.g., embryo) and one or both parents. Genotype imputation involves phasing genotypes at genotyped SNV positions from the sequence data and a reference panel of haplotypes of fully phased individuals with completely determined alleles, followed by matching haplotypes which match in the genotyped positions. Publicly available reference panels of known haplotypes (e.g., human haplotypes) include the Haplotype Reference Consortium dataset, which contains phased SNV genotypes coded in the human genome assembly GRCh37, and the 1000 Genomes Project. Methods for genotype imputation are known in the art and include, for example, Beagle (see, e.g., Browning et al. (2018) Am J Hum Genet 103(3):338-348, Browning and Browning (2007) Am J Hum Genet 81:1084-1097, MACH (see, e.g., Li et al. (2009) Ann Rev Genom Hum Genet 10:387-406, Li et al. (2010) Genet Epidemiol 34:816-834.

In various embodiments of the method of FIG. 1, imputing of missing variant data and phasing of chromosomal haplotypes is performed using Beagle version 5.0. The Beagle program does not make any assumptions about relatedness between genomic samples. Although this may lead to a relative reduction in accuracy of recovery of variants and proper phasing for genomic samples with known relationships compared to other methods, one advantage is that in the event of unrelated samples (e.g. incorrectly labeled parent/offspring sample), Beagle will not attempt to enforce a relationship on its analysis. Additionally, Beagle version 5 is relatively quick compared to some other programs. Imputation and phasing performance of imputation may be limited by the availability of relevant pre-phased haplotype data in the database. In some embodiments of the method of FIG. 1, the imputation process is performed using the Phase 3 1000 Genomes haplotype reference database containing haplotypes from 2,504 subjects. Augmentation of reference databases with additional sequence variant data may improve haplotype inference for a specific target population. The incorporation of imputation in some embodiments of methods and systems provided herein yields a fully phased and complete set of alleles and/or haplotypes predicted for one or both parents and an offspring, e.g., embryo. This information is then used in determining ratios of maternal and/or paternal contribution of alleles to the embryo which are used in detecting and/or identifying a genomic feature and/or assessing, inferring or determining patterns of inheritance (POI) of genomic features, e.g., aneuploidy and polyploidy.

The fully phased and complete set of inferred alleles and/or haplotypes of variants (SNV-containing sequences) determined in step 105 of the method of FIG. 1 is used to classify genetic abnormalities of an offspring (i.e., abnormalities that were previously identified in step 104A) as either being maternal or paternal in origin in step 106A or step 107 of the method depicted in FIG. 1. As shown in FIG. 1, if the karyogram for an offspring (e.g., embryo) indicates that aneuploidy is present in the embryo, then the method proceeds to step 106A for analysis and determination of pattern of inheritance. If the karyogram for an offspring indicates that aneuploidy is not present or unbalanced-sex polyploidy is present in the offspring, the method proceeds to step 106B to first determine if the offspring exhibits a genome-wide dosage imbalance and is polyploid and then to step 107 for a determination of the pattern of inheritance of the polyploidy if a polyploidy is detected. If the karyogram indicates that a sample is male or female with aneuploidy and polyploidy had not been detected, the analysis proceeds from step 105 to 106A to determine the parent of origin of the aneuploidy. Then, the analysis proceeds to step 106B to estimate the maternal and paternal contributions to the embryo and detect any balanced-sex polyploidy. If a balanced-sex polyploidy is not detected, the analysis ends for the sample. If, however, a balanced-sex polyploidy is detected, the analysis proceeds to step 107 to determine the parent of origin of the polyploidy. If the karyogram indicates that the sample has an unbalanced-sex polyploidy or is female with no meiotic aneuploidy, it proceeds to step 105 and continues through step 106B to estimate maternal and paternal contributions to the embyro and identify the parent of origin of any aneuploidy and then proceeds to step 107 to determine the parent of origin of the polypolypioidy, A limitation of Beagle version 5.0 imputation program is that it assumes that all chromosomes analyzed are diploid and returns imputed data accordingly. As such haploid data is generally coded as homozygous diploid. Triploid (and more complex) haplotypes are similarly imputed as diploid. In such cases, the pattern of inheritance analysis described herein is not based on a presumed correct set of inferred haplotypes but on the frequencies of SNV-containing variants identified in the low-coverage and/or low-depth (e.g., low resolution) sequencing data and their dose relationship to parents, as described herein. Specifically, phased and imputed data are treated as pseudo chromosomes and, if truly aneuploid, are expected to be identical and to match either maternal or paternal genotypes, not both, at least for informative variants. The workflow of an exemplary method 200 used in one embodiment of the pattern of inheritance (POI) determination step 106A or step 107 is depicted in FIG. 2.

In the classification of an embryo abnormality (e.g., aneuploidy and/or polyploidy) as being of maternal or paternal origin in step 106A or step 107 of the embodiment of the method of FIG. 1, the measure of relatedness of offspring, e.g., embryo, genomic DNA to both the mother and father is calculated. In one embodiment, the calculation involves the counting of the total variants identified in each defined genomic bin (defined region of the genome, e.g., 1 million bases) in the offspring, e.g., embryo, shared with the mother or with the father, and converting the counts into a single relatedness value per genomic region of a user-defined size. Prior to counting, the input allele/haplotype variant sequence data are filtered (see step 201 of FIG. 2). Input data is expected to be imperfect given that low pass sequence data, especially from certain sequencers, generally includes a large number of sequencing artifacts. Therefore, the first step in the counting process is to filter detected variants. Specifically, in some embodiments, the following sequences are identified and excluded from counting: (1) sequences of sites with any missing alleles between the offspring, mother and father (trio) (inability to infer relatedness in such cases), (2) sequences of sites with constant alleles across a trio (non-informativeness), (3) sequences of sites with a novel allele within one individual in the trio (non-informativeness and likelihood of sequencing artifact), and (4) sequences of sites that are consistent with euploid inheritance only (non-informative for aneuploid relationship estimation). Filtering can also include excluding SNPs that are inconsistent with Mendelian inheritance. In this embodiment of the method of FIG. 2, the input variants are filtered indirectly (i.e., by comparing relationships between offspring and parents). This method presumes correct trios and does not necessarily filter the correct sites in the event of an incorrectly specified parent.

Figure 2:
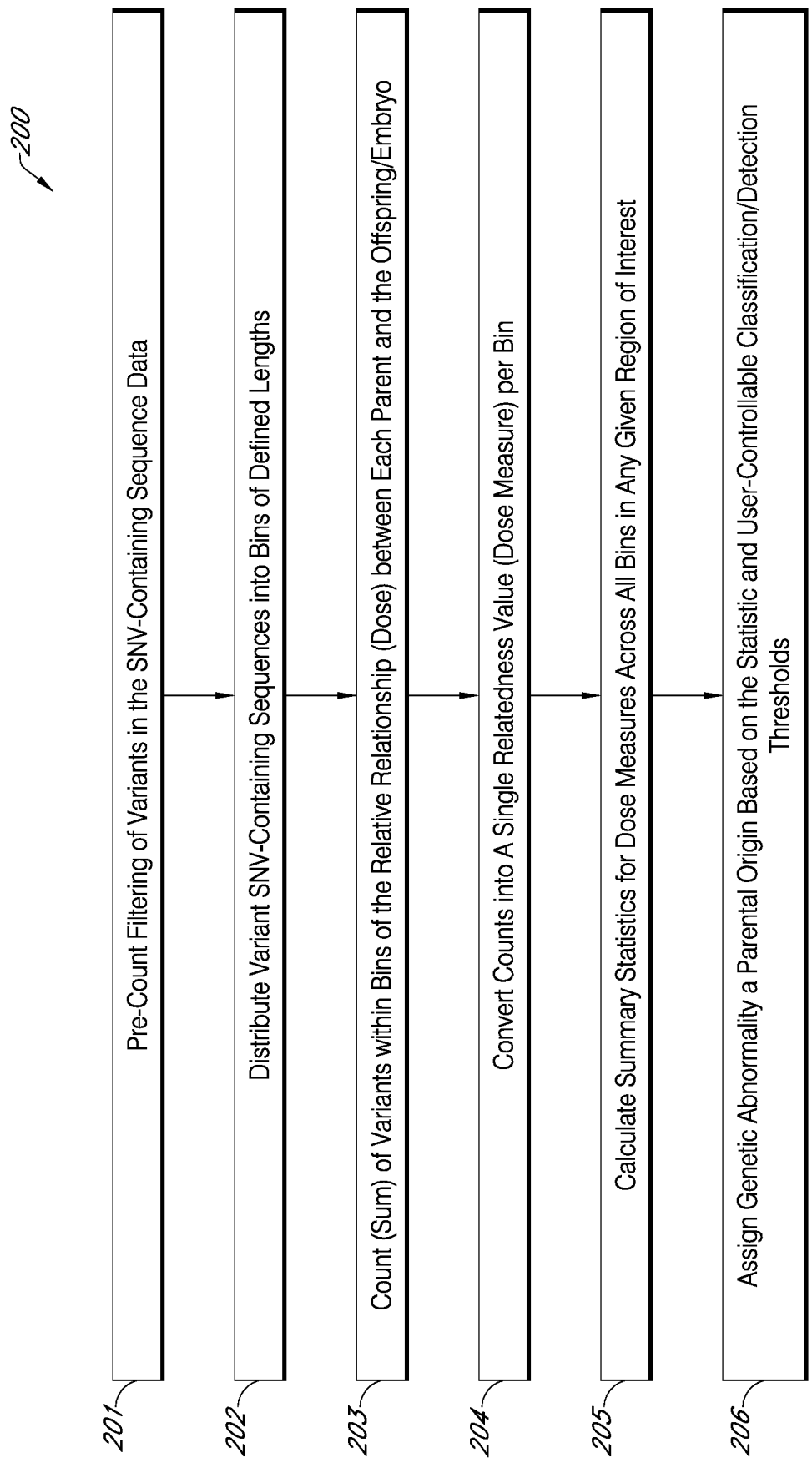
FIG. 2 is an exemplary flowchart showing a method for classifying genetic abnormalities of an offspring, e.g., embryo, as either being maternal or paternal in origin and determining pattern of inheritance (POI), in accordance with various embodiments.

After the variants are filtered (generally down to about 10% of the input observed phased/imputed SNV-containing variants), the remaining variants are distributed into bins of a user-defined size by genomic regions withing individual chromosomes (e.g., 1 million bases) (step 202 of FIG. 2).

In step 203 of FIG. 2, variants within each defined bin are counted and two values are generated for each bin. The first value is the number of variants phased together between the offspring and maternal component and the second value is the number of variants phased together between the offspring and the paternal component. To determine inheritance for individual chromosome aneuploidy only the bins known to be aneuploidy (based on the bins associated with the aneuploid CNV call) are assessed for that particular aneuploidy. These include a set of counts not reported in the results file such as: (a) OvM (i.e. "offspring variants shared with maternal source") which is a count of alternate (i.e., non-reference) alleles shared between the embryo and the mother, and (b) OvP (i.e. "offspring variants shared with paternal source"), which is a count of alternate alleles shared between the embryo and the paternal sample. Reference alleles match the reference genome and generally it is expected that the majority of alleles match the reference genome. An alternate allele is one that for any given locus there is a variant that does not match the reference genome. Because a great majority of the bases/allele match the reference genome for the mother, father and offspring, the reference alleles are less informative. Only alternate alleles are used because reference alleles are generally non-informative.

The output of the counting functions of step 203 is a set of OvM and OvP counts, per bin, across all chromosomes in the specified analysis (only the specific chromosome(s) of the aneuploidy for offspring having an aneuploid karyotype or all chromosomes for an embryo having a karyotype that is not indicative of aneuploidy but correlates with polyploidy). In step 204 of FIG. 2, these counts are converted into a single relatedness value, referred to as a dose measure, per bin. Two statistics are calculated within each bin: (1) L2RAT which is $$\log_2\left(\frac{OvM + s}{OvP + s}\right),$$

where OvM and OvP are the counts, and s is the SMOOTH controllable element (provided either in a configuration file or via command line argument). The smoothing parameters is used to prevent infinite values in the case of bins with zero counts. Values between 1 and 30 are reasonable (larger values shrink the estimate), and (2) DIFF which is defined as OvM−OvP. In some embodiments L2RAT is the default dose measure and is more robust to outliers and can be shrunk as desired. Both estimates are centered at zero (when the offspring shows no stronger relationship to mother or father, and both take positive values when the relationship between offspring is stronger with the mother than the father, and negative values otherwise. In this embodiment, there is an assumption that the dose statistics should be centered at zero for euploid inheritance and that departures from zero beyond that expected by chance indicate stronger relationship (i.e. a greater number of inherited variants) from either the mother or father. This assumption is false in cases where the embryo sample is contaminated with maternal material. In such cases, the dose statistics will be shifted in the positive direction for all chromosomes and therefore may falsely appear polyploid.

In step 205 of FIG. 2, a one sample t-statistic is calculated on the specified dose measure, e.g., L2RAT. The data set for the calculated test statistic is the set of estimated dose values for all bins in the region of interest. For example, if a 10 megabase region was specified and bin size was 1 megabase, then the t-test would be based on 10 L2RAT estimates, one from each bin. In step 205, a test statistic is generated for every provided region of interest (e.g. genome overall, all specified chromosomes, and any specified segmental regions). The number of bins, the mean and standard deviation of the dose statistic, and the p-value and a custom confidence metric are also provided in this step. Choice of both bin size and minimum analyzed region size are user controllable. Because inferred haplotypes are large, small bin sizes are not optimal as neighboring regions are correlated and subsequently the counts in small adjacent bins are likely to be correlated as well. This could lead to t-statistics with a larger variance than desired (i.e. they could produce larger t-test values, both positive and negative, than warranted).

In step 206 of FIG. 2, each genetic abnormality, e.g., aneuploidy, is assigned a parental origin using the t-statistic and user-controllable classification/detection thresholds. The parental origin determination is based on the number of parental-offspring allele matches for all chromosomes (genome level association, e.g., in the case of polyploid offspring) and at the individual chromosome level (in the case of aneuploid offspring). Thus, at the meiotic aneuploidy level (both whole and partial chromosomes) only the alleles present in that chromosome correlated with the aneuploidy are considered when making the comparison of likeness. In the case where a sample is polyploid and aneuploid, known chromosomal aneuploidies are classified for parental origin based on the full chromosome test statistic. The number of bins in the test will depend on both the bin size and the chromosome length (the analysis will have greater statistical power to classify aneuploidies for longer chromosomes). The output for such a test will either be: "maternal," "paternal," or "not classified." An output of "not classified" is returned when the test statistic fails to exceed a user controllable threshold (CLASS_THRESHOLD_ANEUPLOID). Although these categories are fixed, the specific messages returned are user controllable. In the case where an embryo sample is not polyploid, known segmental aneuploidies (that meet a user controllable size requirement) are classified based on the regional test statistic. The number of bins in the test will depend on both the bin size and the region size (there is greater statistical power to classify aneuploidies for longer regions). The output for such a test will either be: "maternal," "paternal," or "not classified." An output of "not classified" is returned when the test statistic fails to exceed the user controllable threshold (CLASS_THRESHOLD_ANEUPLOID). Although these categories are fixed, the specific messages returned are user controllable.

Returning to FIG. 1, in step 106B, the maternal and paternal contributions to the entire genome (i.e., all chromosomes) of the offspring, e.g., embryo, are estimated based on the number of shared variant alleles and are used in detecting any previously undetected polyploidy or to confirm polyploidy detected and identified in the karyograms for the offspring. Step 106B is directly conducted after step 105 for any offspring that were not identified as aneuploid through the earlier karyotyping process (with the exception, in some embodiments, of diploid male embryos) or that show evidence of polyploidy (e.g., unbalanced-sex polyploidy) in the CNV data and karyogram. In some embodiments, if the offspring was identified as a diploid male (46,XY) it is not assessed for polyploidy or pattern of inheritance. Additionally, all aneuploid offspring evaluated for pattern of inheritance in step 106A of FIG. 1 undergo analysis in step 106B of the maternal and paternal contributions to the entire genome (i.e., all chromosomes) of the offspring to determine if there is any undetected polyploidy. This step is performed only where the offspring sample is not previously reported as "polyploid" (and, in some embodiments, where the sample is also not male). The output for such a test will either be: "maternal," "paternal," or "not detected." An output of "not detected" is returned when the test statistic fails to exceed a user controllable threshold (DETECT_THRESHOLD_POLYPLOIDY). Although these categories are fixed, the specific messages returned are user controllable. A higher threshold for polyploidy detection is set than for classification of parental origin of polyploidy, even for full genome analysis. In the case of a known (as identified in the initial karyograms) non-euploid offspring sample, parental origin of polyploidy is classified based on the full genome test statistic in step 107 of FIG. 1. The number of bins in the test will depend on the bin size. The output for such a test will either be: "maternal," "paternal," or "not classified." An output of "not classified" is returned when the test statistic fails to exceed the user controllable threshold (CLASS_THRESHOLD_POLYPLOID). Although these categories are fixed, the specific messages returned are user controllable.

Figure 3:
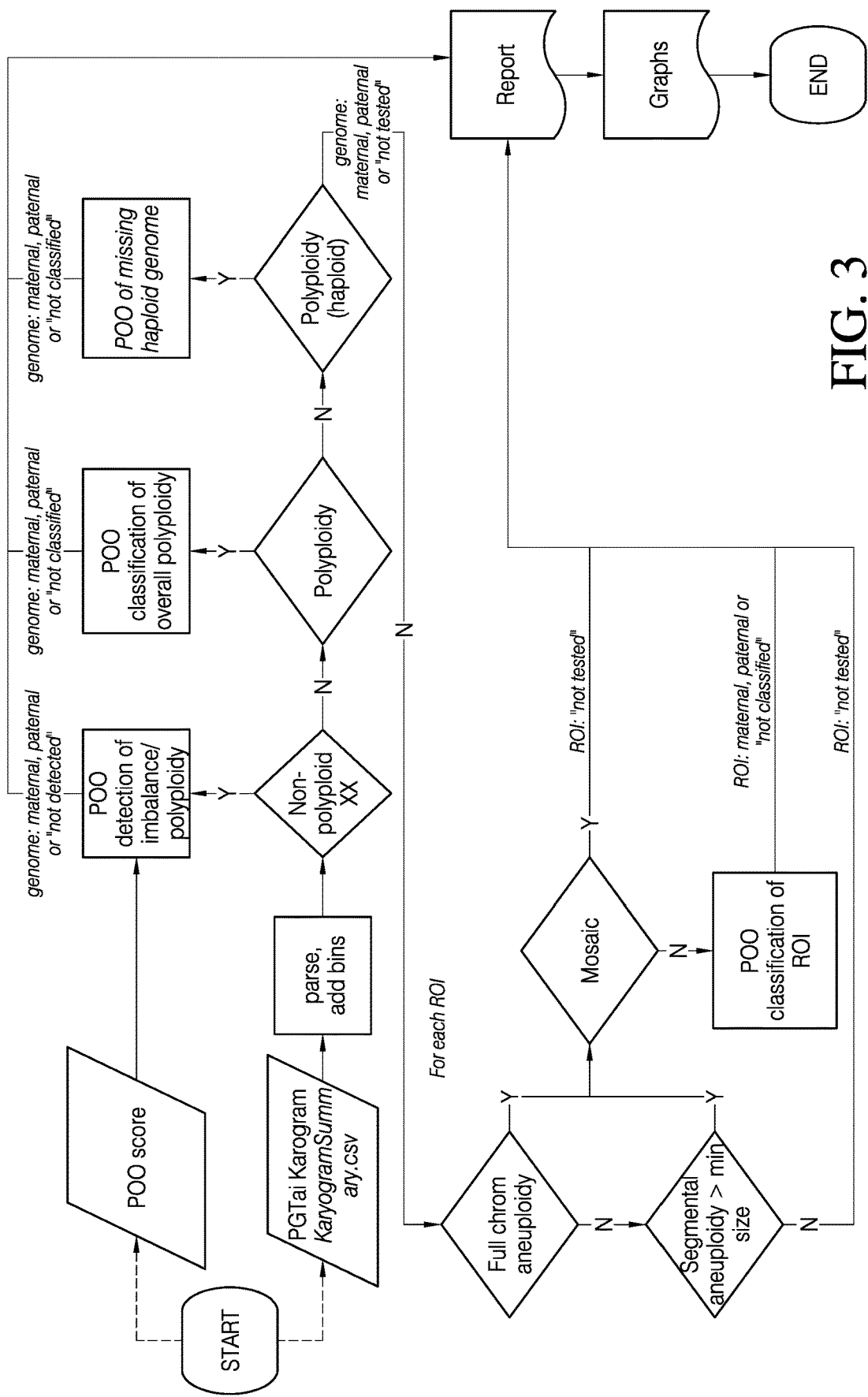
FIG. 3 is a decision tree diagram depicting a logical flow for conducting some embodiments of the methods for detecting and/or classifying the parental origin of genetic abnormalities provided herein, in accordance with various embodiments.

FIG. 3 is a decision tree diagram depicting a logical flow for conducting some embodiments of the methods for detecting and/or classifying the parental origin of genetic abnormalities provided herein. This diagram depicts, for some embodiments of the method, the process of determining the final result for any specimen being tested by the embodiment and is referred to as the Parent of Origin (POO) pipeline. In some embodiments, testing for an offspring, e.g., embryo, DNA sample proceeds down the decision path as follows. If a sample is a non-polyploid female (XX), it is assessed by the method to determine if the genome dosage significantly deviates from expected, and, if so, it is characterized as polyploid (maternal or paternal) and reported. If a sample is not a non-polyploid XX and is called polyploid (XXY or XYY), then it enters the pipeline for characterization of the pattern of inheritance (POI) for polyploidy and is then reported. If a sample is neither a non-polyploid XX or a polyploid XXY or XYY and is called haploid by CNV analysis, it enters the pipeline for assessment of genome-wide dosage imbalance and is reported. All other samples that do not meet the criteria listed previously are assessed for full chromosome aneuploidies and segmental chromosome aneuploidies. If these are mosaic aneuploidies as determined by CNV analysis, they are not interrogated by the method. If they are whole copy changes (meiotic aneuploidy), the method attempts to classify the regions of interest as maternal, paternal or not classified and the result is reported as such.

In various embodiments, methods are provided for assessing, classifying, determining, predicting and/or inferring patterns of inheritance and/or parental origin of one or more genomic features provided herein. The methods can be implemented via computer software or hardware. The methods can also be implemented on a computing device/system that can include a combination of engines for assessing, classifying, determining, predicting and/or inferring patterns of inheritance and/or parental origin of one or more genomic features. In various embodiments, the computing device/system can be communicatively connected to one or more of a data source, sample analyzer, and display device via a direct connection or through an internet connection.

Figure 8:
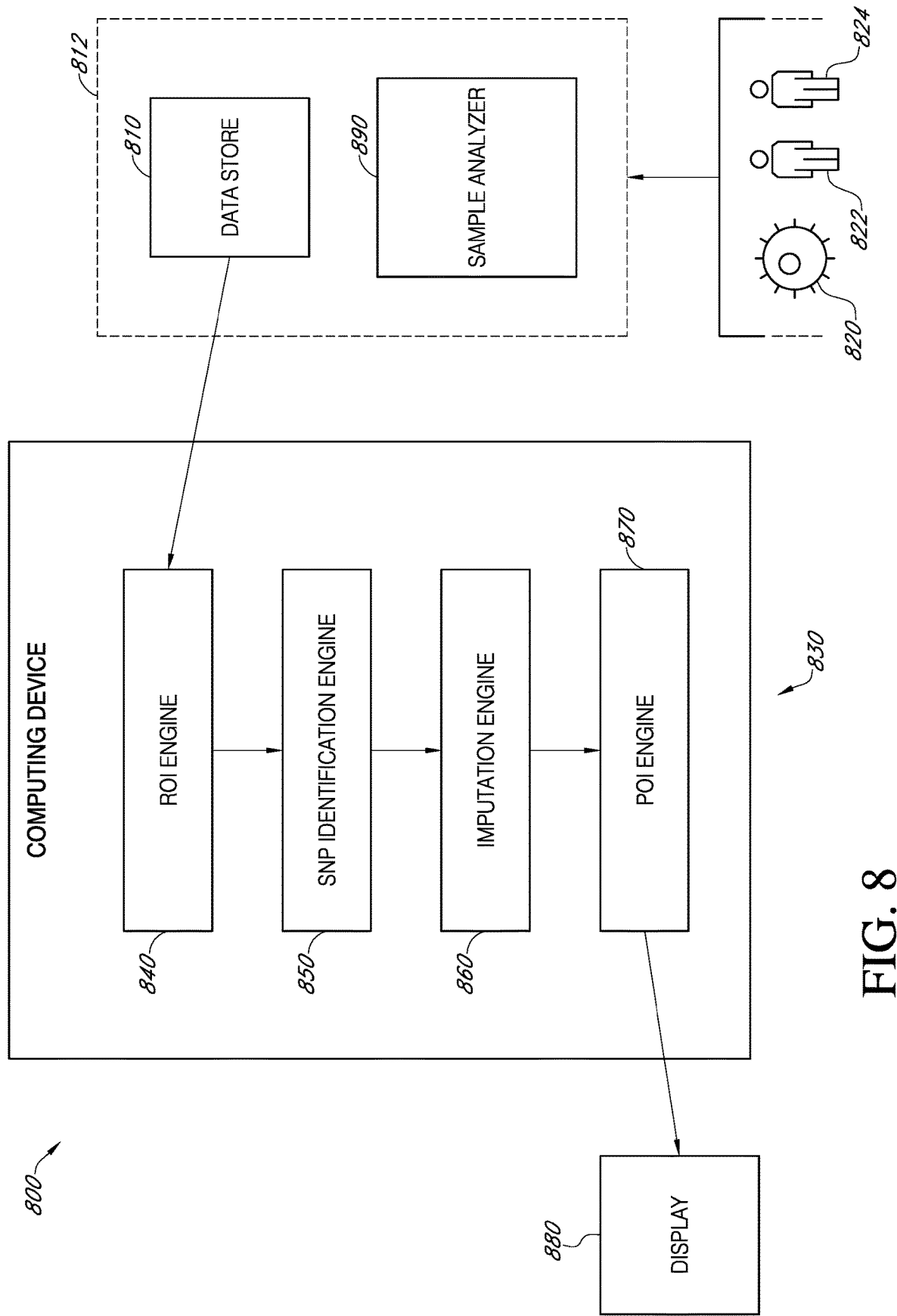
FIG. 8 is a schematic diagram of a system for predicting pattern of inheritance, in accordance with various embodiments.

FIG. 8 is a schematic diagram of a system 800 for determining pattern of inheritance in an embryo (e.g., a human embryo) for a region of interest, in accordance with various embodiments. System 800 can include a data store 810, a computing device 830 and a display 880. System 800 can also include a sample analyzer 890.

The sample analyzer 890 can be communicatively connected to the data store 810 by way of a serial bus (if both form an integrated instrument platform 812) or by way of a network connection (if both are distributed/separate devices). The sample analyzer 890 can be configured to analyze samples from an embryo 820, a mother 822 and a father 824. Sample analyzer can be a sequencing instrument, such as a next generation sequencing instrument, configured to sequence samples to collect sequencing data for further analysis. In various embodiments, the sequencing data can then be stored in the data store 810 for subsequent processing. In various embodiments, the sequencing datasets can be fed to the computing device 830 in real-time. In various embodiments, the sequencing datasets can also be stored in the data store 810 prior to processing. In various embodiments, the sequencing datasets can also be fed to the computing device 830 in real-time.

The data store 810 can be communicatively connected to the computing device 830. In various embodiments, the computing device 830 can be communicatively connected to the data store 810 via a network connection that can be either a "hardwired" physical network connection (e.g., Internet, LAN, WAN, VPN, etc.) or a wireless network connection (e.g., Wi-Fi, WLAN, etc.). In various embodiments, the computing device 830 can be a workstation, mainframe computer, distributed computing node (part of a "cloud computing" or distributed networking system), personal computer, mobile device, etc.

Data store 810 can be configured to receive embryo, maternal and paternal sequence data, wherein the maternal sequence data is from a mother of the embryo and the paternal sequence data is from a father of the embryo. In various embodiments, at least one of the embryo, maternal and paternal sequence data is acquired by low-coverage sequencing. The low-coverage sequencing can be between about 0.001 and 10×. The low-coverage sequencing can be between about 0.01 and 0.5×. The low-coverage sequencing can be between about 0.25 and 0.2×.

Computing device 830 can further include a region of interest engine (ROI engine) 840, a single nucleotide polymorphism identification engine (SNP identification engine) 850, an imputation engine 860 and a pattern of inheritance engine (POI engine) 870. As stated above, computing device 830 can be communicatively connected to data store 810.

ROI engine 840 can be configured to align the received sequence data to a reference genome and identify a region of interest in the aligned embryo sequence data. The region of interest can be genome wide. The region of interest can be an observed copy number variation.

SNP identification engine 850 can be configured to identify single nucleotide polymorphisms (SNPs) in the maternal sequence data, paternal sequence data, and the identified region of interest in the embryo sequence data.

Imputation engine 860 can be configured to filter at least one of the embryo, maternal and paternal sequencing data to remove sequencing artifacts impute missing gaps in the maternal sequence data and the paternal sequence data using an imputation reference. The imputation reference can comprise at least 1000 genomes.

Imputation engine 860 can be further configured to filter at least one of the embryo, maternal and paternal sequencing data to remove sequencing artifacts. The filtering can comprise excluding sequences of sites with any missing alleles between the embryo, mother and father. The filtering can comprise excluding sequences of sites with constant alleles across between the embryo, mother and father. The filtering can comprise excluding sequences of sites with a novel allele within one of the embryo, mother and father. The filtering can comprise excluding sequences of sites that are consistent with euploid inheritance. Filtering can also include excluding SNPs that are inconsistent with Mendelian inheritance.

POI engine 870 can be configured to count the number of SNPs that are common between the embryo and the mother in the identified region of interest for the embryo sequence data and a corresponding region on the maternal sequence data to determine a maternal contribution value. POI engine 870 can be configured to count the number of SNPs that are common between the embryo and the father in the identified region of interest for the embryo sequence data and a corresponding region on the paternal sequence data to determine a paternal contribution value. POI engine 870 can be configured to classifying a pattern of inheritance for the embryo as maternal or paternal based on the relative contribution values between mother and father.

POI engine 870 can be further configured to count SNPs across the entire genome to determine the maternal and paternal contribution values and determine if the embryo is polyploid. When the embryo is polyploid, POI engine 870 can be further configured to classify a pattern of inheritance for the polyploid as maternal or paternal based on the relative contribution values between mother and father.

After the pattern of inheritance for the embryo has been classified, it can be displayed as a result or summary on a display or client terminal 880 that is communicatively connected to the computing device 830. In various embodiments, display 880 can be a thin client computing device. In various embodiments, display 880 can be a personal computing device having a web browser (e.g., INTERNET EXPLORER™, FIREFOX™, SAFARI™, etc.) that can be used to control the operation of the region of interest engine (ROI engine) 840, the single nucleotide polymorphism identification engine (SNP identification engine) 850, the imputation engine 860, and the pattern of inheritance engine (POI engine) 870.

It should be appreciated that the various engines can be combined or collapsed into a single engine, component or module, depending on the requirements of the particular application or system architecture. In various embodiments the region of interest engine (ROI engine) 840, the single nucleotide polymorphism identification engine (SNP identification engine) 850, the imputation engine 860, and the pattern of inheritance engine (POI engine) 870 can comprise additional engines or components as needed by the particular application or system architecture.

Figure 9:
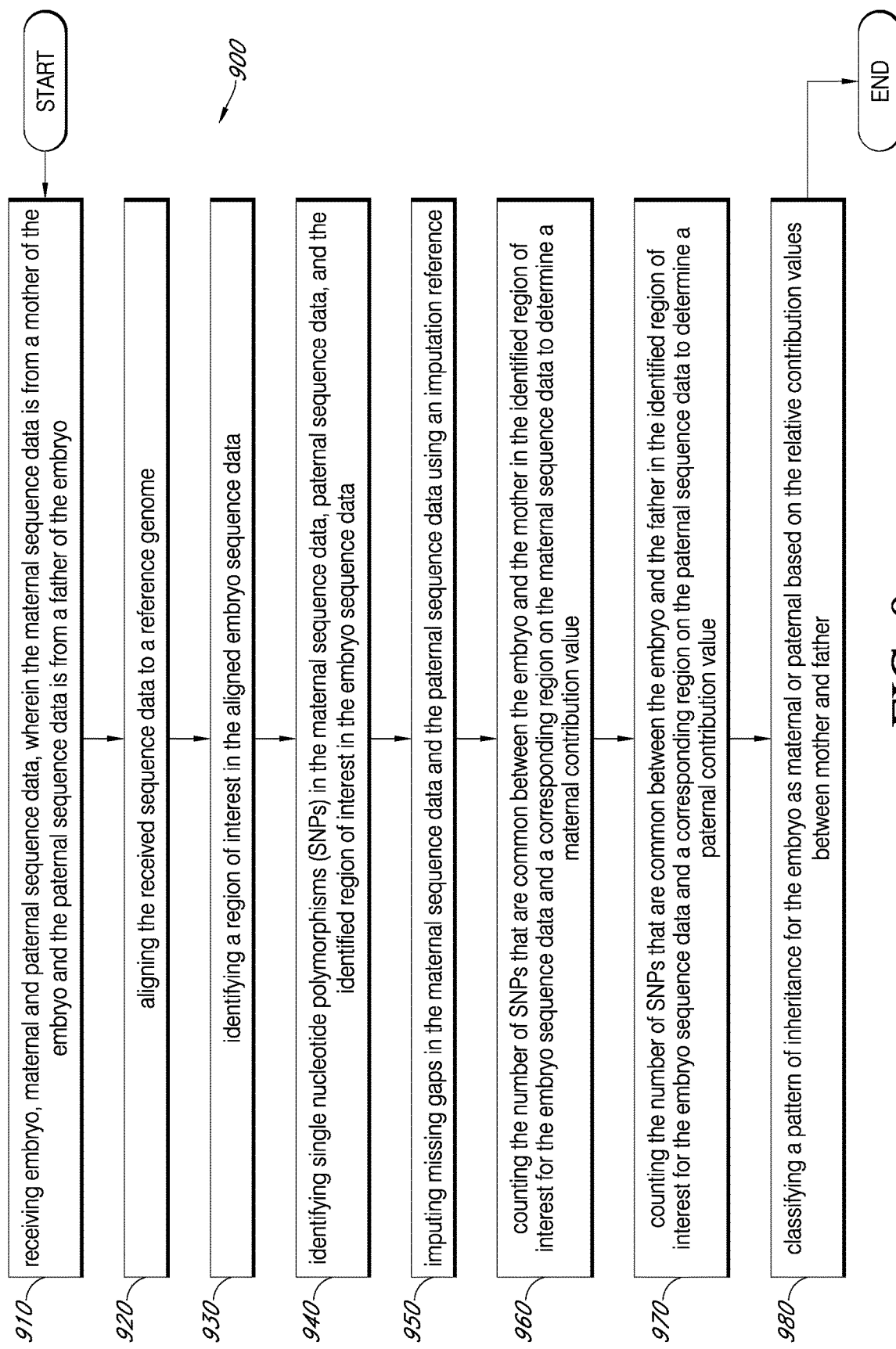
FIG. 9 is an exemplary flowchart showing a method for pattern of inheritance, in accordance with various embodiments.

FIG. 9 is an exemplary flowchart showing a method 900 for determining pattern of inheritance in an embryo for a region of interest, in accordance with various embodiments.

In step 910, embryo, maternal and paternal sequence data is received, wherein the maternal sequence data is from a mother of the embryo and the paternal sequence data is from a father of the embryo. In various embodiments, at least one of the embryo, maternal and paternal sequence data is acquired by low-coverage sequencing. The low-coverage sequencing can be between about 0.001 and 10×. The low-coverage sequencing can be between about 0.01 and 0.5×. The low-coverage sequencing can be between about 0.25 and 0.2×.

In step 920, the received sequence data is aligned to a reference genome.

In step 930, a region of interest in the aligned embryo sequence data is identified. The region of interest can be genome wide. The region of interest can be an observed copy number variation.

In step 940, single nucleotide polymorphisms (SNPs) in the maternal sequence data, paternal sequence data, and the identified region of interest in the embryo sequence data are identified.

In step 950, missing gaps in the maternal sequence data and the paternal sequence data are imputed using an imputation reference. The imputation reference can comprise at least 1000 genomes. In various embodiments, step 950 can also include filtering at least one of the embryo, maternal and paternal sequencing data to remove sequencing artifacts. The filtering can comprise excluding sequences of sites with any missing alleles between the embryo, mother and father. The filtering can comprise excluding sequences of sites with constant alleles across between the embryo, mother and father. The filtering can comprise excluding sequences of sites with a novel allele within one of the embryo, mother and father. The filtering can comprise excluding sequences of sites that are consistent with euploid inheritance. Filtering can also include excluding SNPs that are inconsistent with Mendelian inheritance.

In step 960, the number of SNPs that are common between the embryo and the mother in the identified region of interest for the embryo sequence data and a corresponding region on the maternal sequence data are counted to determine a maternal contribution value.

In step 970, the number of SNPs that are common between the embryo and the father in the identified region of interest for the embryo sequence data and a corresponding region on the paternal sequence data are counted to determine a paternal contribution value.

In step 980, a pattern of inheritance for the embryo is classified as maternal or paternal based on the relative contribution values between mother and father.

In various embodiments, the method can further include counting SNPs across the entire genome to determine the maternal and paternal contribution values and determine if the embryo is polyploid. When the embryo is polyploid, a pattern of inheritance for the polyploid can be classified as maternal or paternal based on the relative contribution values between mother and father.

EXAMPLES

Example 1—Classification of Parental Origin of Monosomy

DNA extracted from a human embryo having a known karyotype 42;XY;−14;−15;−19;−21 and DNA samples from both parents were sequenced using a NextSeq sequencing system (Illumina) at 0.1× coverage. Sequence reads were aligned using the Bowtie2 alignment program and mapped to a human reference genome (HG19). The total number of reads in each 1-million base pair bin were counted. The data were normalized based on GC content and depth and tested against a baseline generated from samples of known outcome. Statistical deviations from a copy number of 2 were reported (if present, if not=euploid) as aneuploidy. A karyotype of 42;XY;−14;−15;−19;−21 was determined. SNVs in the sequencing data were identified using methods as described herein. Imputing of missing variant data and phasing of chromosomal haplotypes was performed using the SNV data from the embryo and each parent and the Beagle version 5.0 imputation program using the Phase 3 1000 Genomes haplotype database as a reference panel. The measure of relatedness of embryo genomic DNA to both the mother and father was calculated as described herein by counting variants in the embryo shared with the mother and with the father and converting the counts into a single relatedness value per genomic region of a user-defined size.

Figure 4:
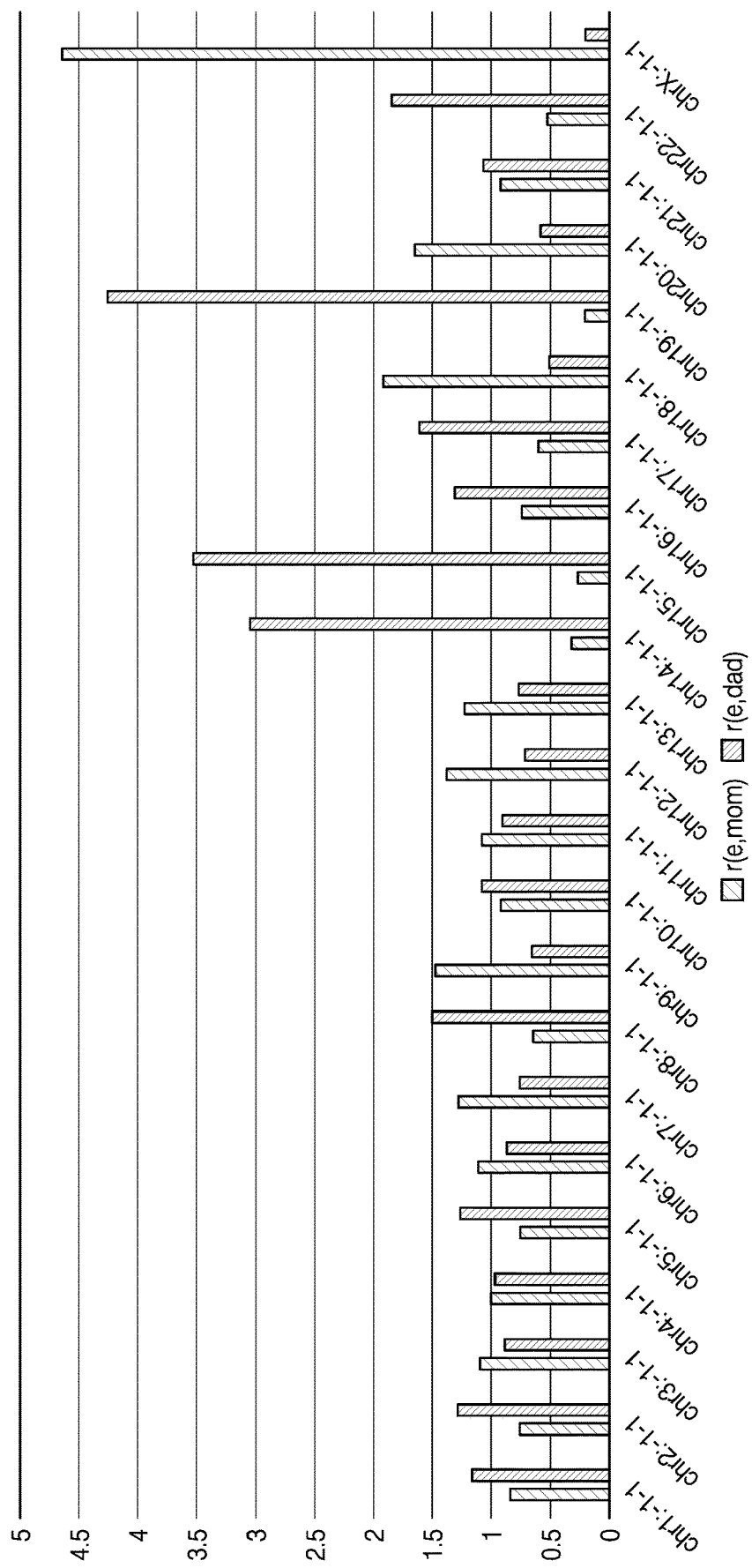
FIG. 4 is a bar graph depicting the ratio of the variant alleles of the mother that matched variant alleles of a monosomic embryo out of the total variant alleles analyzed per chromosome (blue bars) compared to the ratio of the variant alleles of the father that matched variant alleles of the embryo out of the total variant alleles analyzed per chromosome (orange bars), in accordance with various embodiments.

The results of the analysis are depicted in the bar graph shown in FIG. 4. For each of the 22 autosomal chromosomes and the X chromosome (x-axis of graph is chromosome number), FIG. 4 shows the ratio of the variant alleles in that chromosome that matched the mother (blue bars) and the ratio of variant alleles that matched the father (orange bars) (the y-axis is the ratio of embryo variant alleles that matched with either given parent). A comparison of the ratio of matching variant alleles shows that on average for most of the chromosomes (other than the X chromosome of this XY male embryo), the ratio of matching alleles for the mother and father are fairly similar. However, for chromosomes 14, 15, 19, and 21, the ratio of matching alleles for the father is higher than the ratio of matching alleles for the mother. Furthermore, the overall proportion of counts (the ratio of matching alleles to total variant alleles) of the number of informative alleles matching the father is higher than those matching the mother. These results indicate that the four chromosomal deletions are maternal in origin and are indicative of a maternal pattern of inheritance of monosomy.

Example 2—Classification of Parental Origin of Trisomy

Figure 5A:
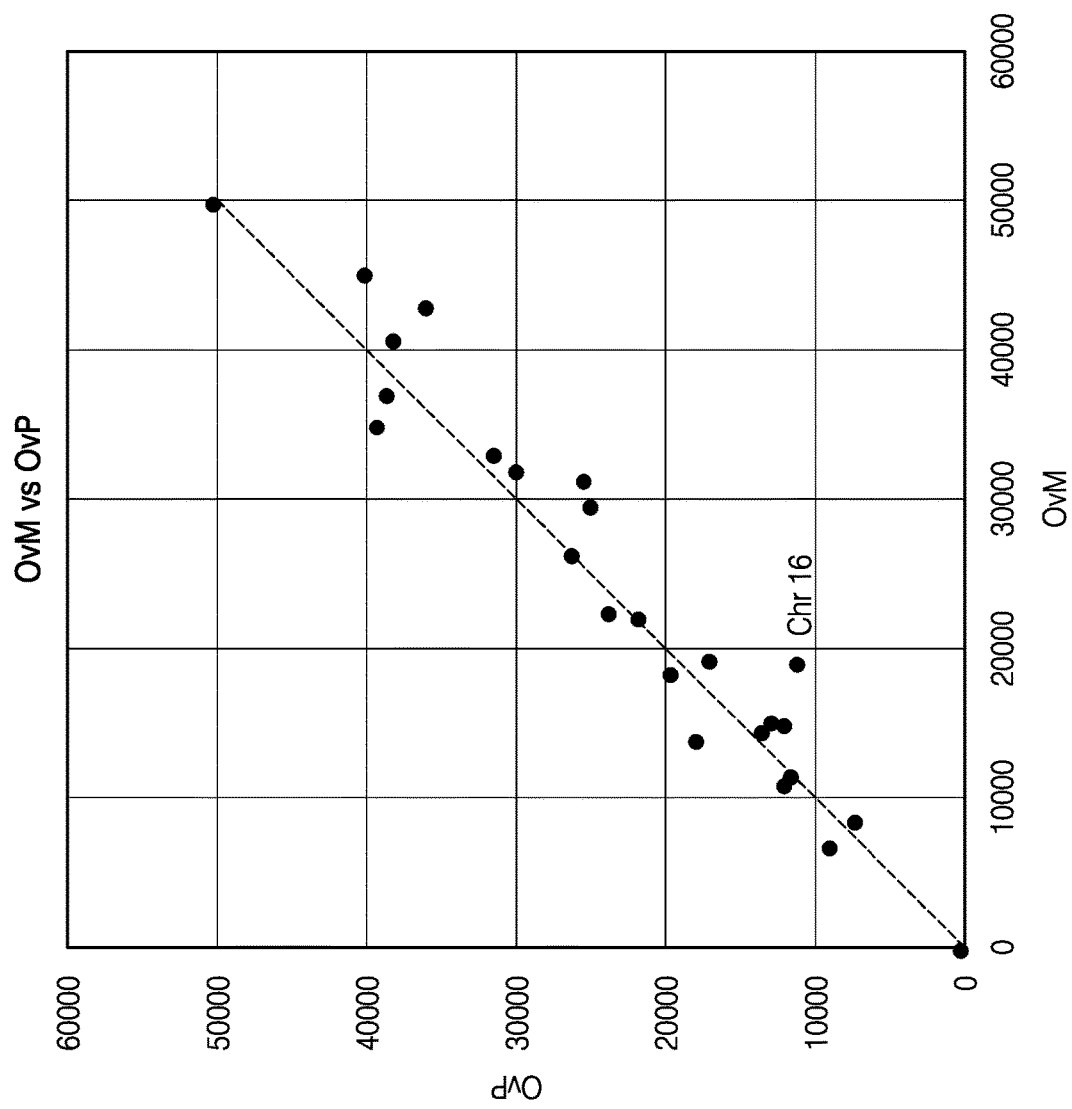
FIGS. 5A and 5B present the results of comparison of the number of variant alleles analyzed of a trisomic embryo that match paternal variant alleles per chromosome to the number of variant alleles analyzed of the embryo that match maternal variant alleles per chromosome, in accordance with various embodiments.
Figure 5B:
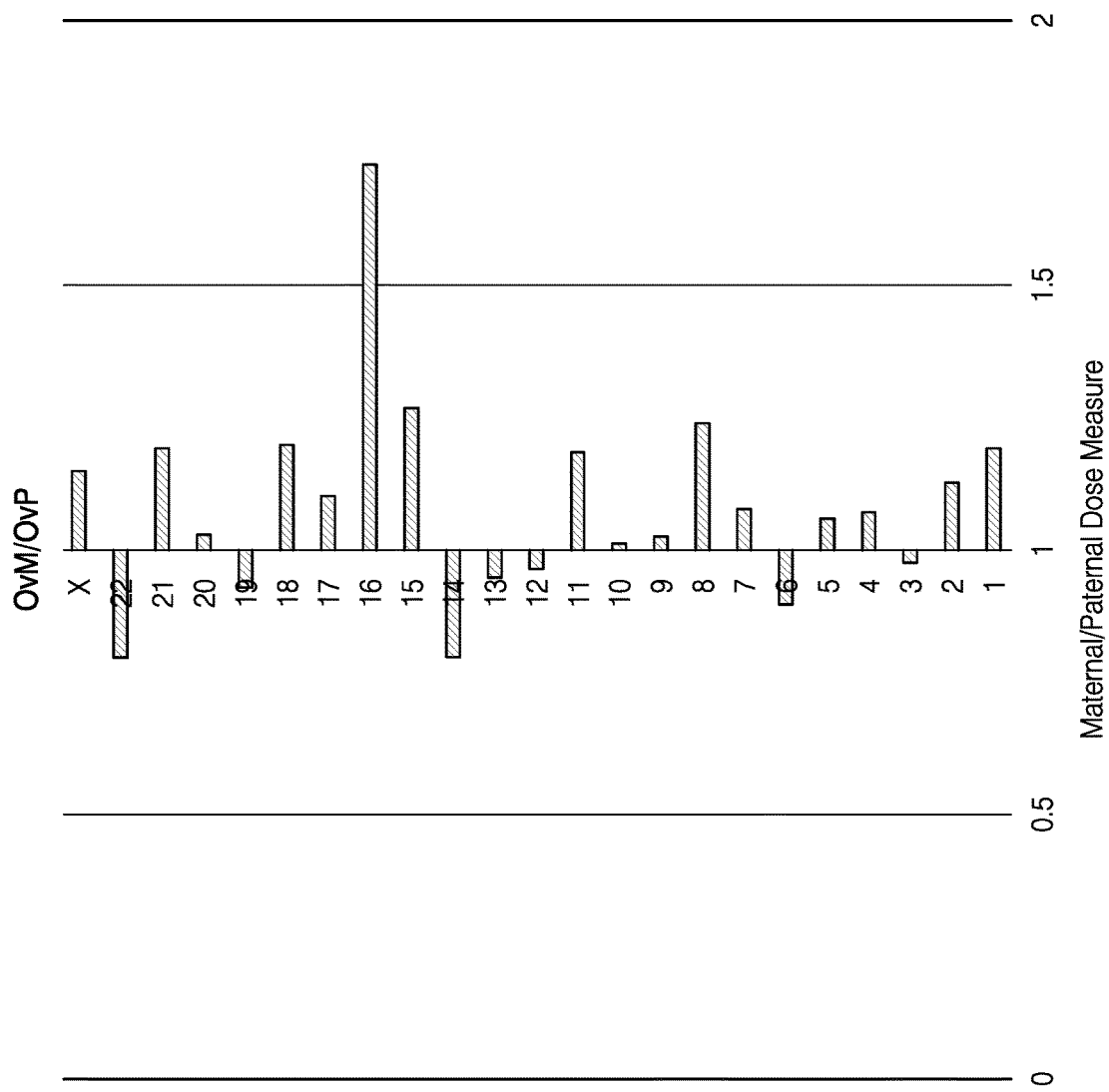

DNA extracted from a human embryo having a known karyotype 47;XX;+16 and DNA samples from both parents were sequenced and analyzed as described in Example 1. FIG. 5A shows a graph of the number of embryo variant alleles shared with paternal source (OvP) vs. the number of embryo variant alleles shared with maternal source (OvM) for each of the 23 chromosomes (blue dots). The dotted diagonal line represents the points on the graph at which the number of embryo variant alleles shared with the maternal source would be equal to the number of embryo variant alleles shared with the paternal source for each chromosome. Dots located above the diagonal line represent chromosomes for which there were more variant alleles shared between the embryo and father than between the embryo and mother. Dots located below the diagonal line represent chromosomes for which there were more variant alleles shared between the embryo and mother than between the embryo and father. As shown in the graph in FIG. 5A, there are more dots below the diagonal line. Furthermore, the dot farthest from the diagonal, which represents counts for shared alleles for chromosome 16, has the greatest ratio (almost 2:1) of counts of shared alleles with mother to shared alleles with father. These results indicate that the additional chromosome 16 in the embryo is of maternal origin and are indicative of a maternal pattern of inheritance of trisomy. FIG. 5B is another graphic presentation of the results shown in FIG. 5A showing the ratio of counts of shared alleles with mother to counts of shared alleles with father per chromosome.

Figure 6:
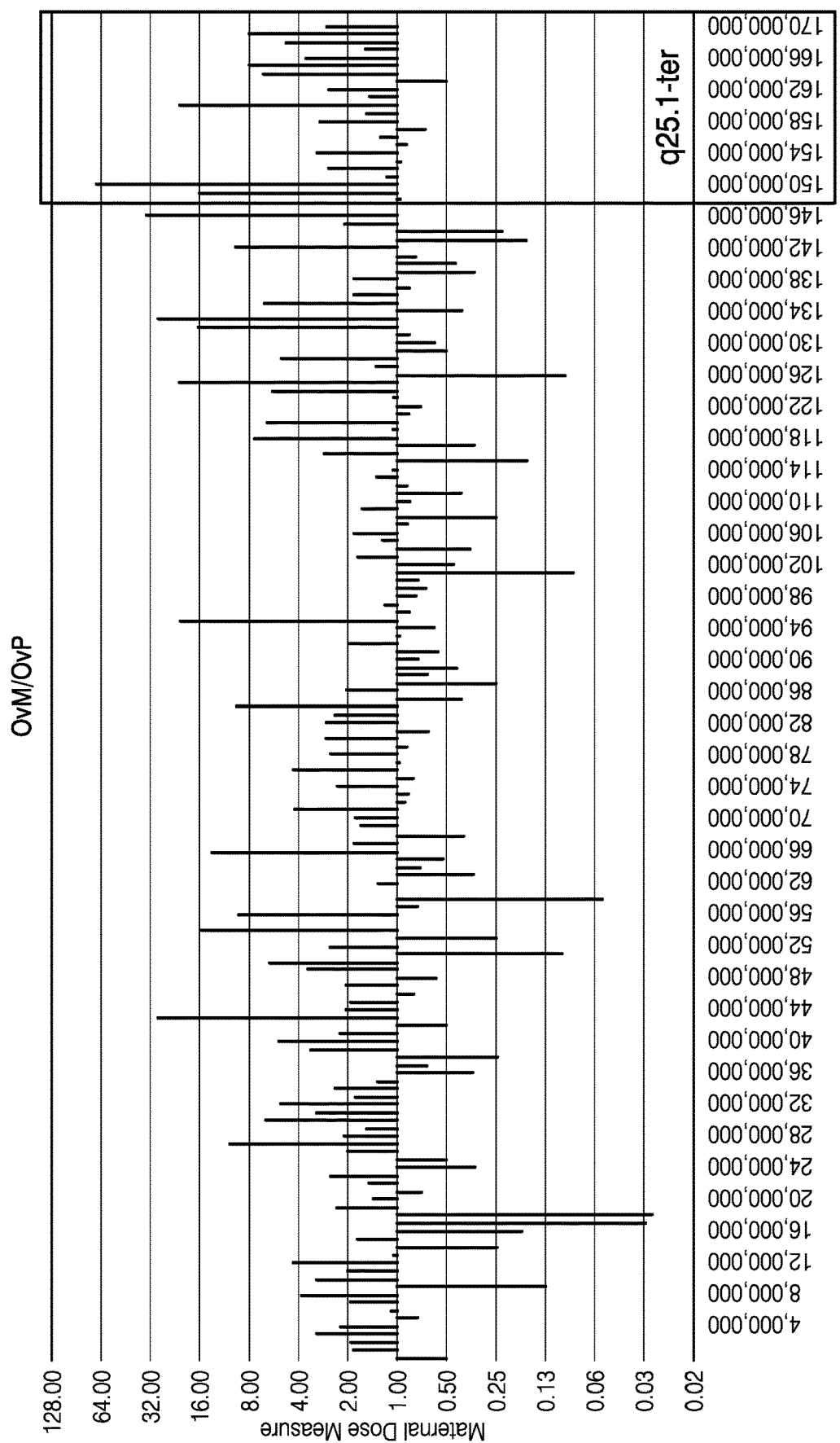
FIG. 6 is a graph showing the ratio (y-axis) of the number of embryo variant alleles shared with maternal source (OvM) to the number of embryo variant alleles shared with paternal source (OvP) with respect to location on chromosome 6 (x-axis in base pairs), in accordance with various embodiments.

Example 3—Classification of Parental Origin of a Segmental Deletion of a Chromosome DNA extracted from a human embryo having a known karyotype 46;XY;del(6)(q25.1-qter);mos33.0% del(6)(pter–q25.1) and DNA samples from both parents were sequenced and analyzed as described in Example 1. The size of the deletion at the p arm of chromosome 6 in the embryo is approximately 20 million bases. The number of variant alleles analyzed for chromosome 6 of the embryo that matched chromosome 6 variant alleles of the mother and of the father were counted in this example. FIG. 6 shows the ratio (y-axis) of the number of embryo variant alleles shared with maternal source (OvM) to the number of embryo variant alleles shared with paternal source (OvP) counts with respect to location on chromosome 6 (x-axis in base pairs). The position of the q arm of the chromosome begins at about 62,000,000 bp and the position of q25.1-ter is located at about 150,000,000 bp. As shown in the graph, the ratio of OvM/OvP from the position at 150,000,000 bp and higher is almost entirely greater than 1.0. These results indicate that the segmental deletion of chromosome 6 is paternal in origin and are indicative of a paternal pattern of inheritance of the deletion.

Example 4—Classification of Parental Origin of Polyploidy

Figure 7:
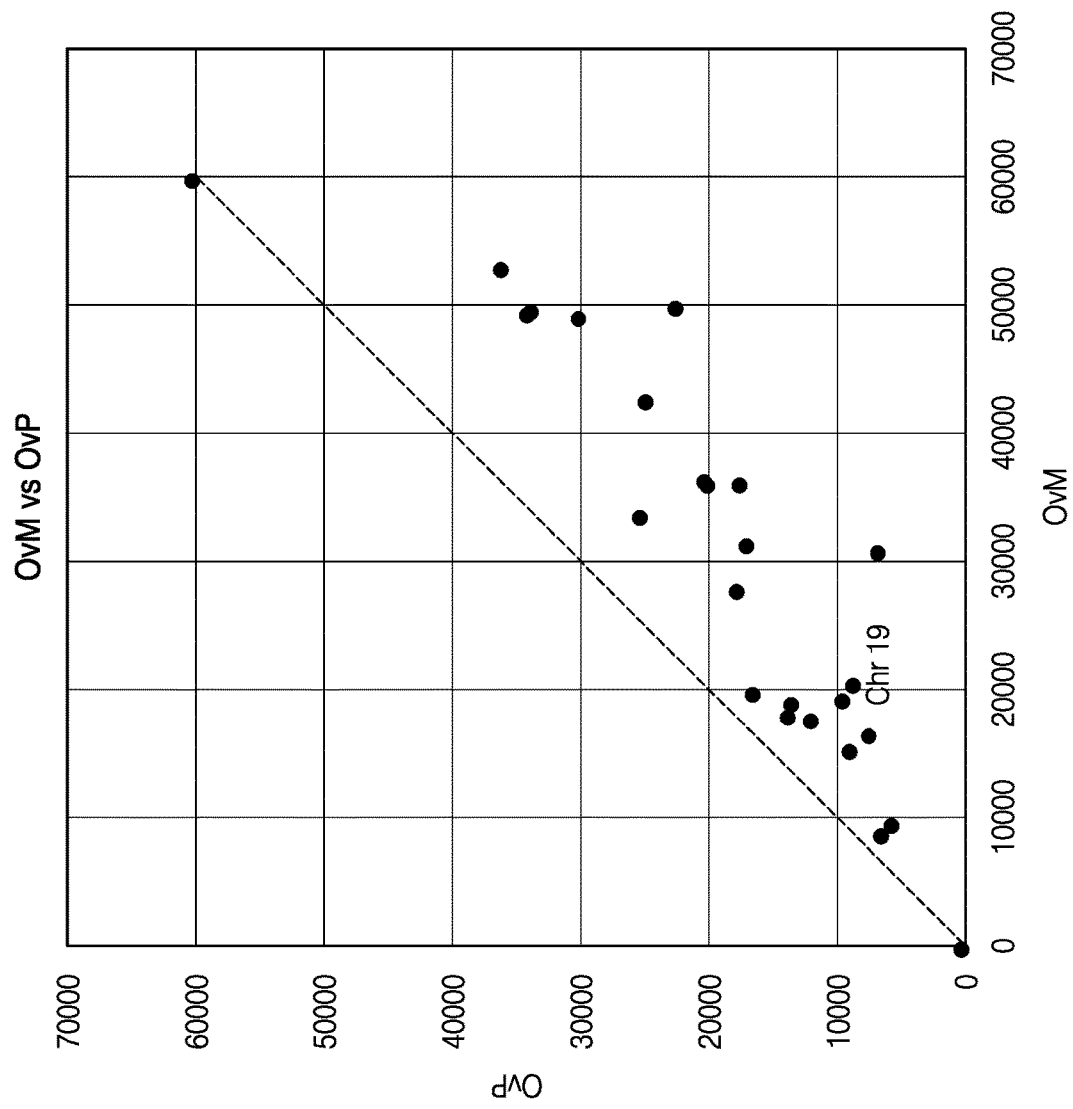
FIG. 7 shows a graph of the number of embryo variant alleles shared with paternal source (OvP) vs. the number of embryo variant alleles shared with maternal source (OvM) for each of the 23 chromosomes (blue dots), in accordance with various embodiments. The dotted diagonal line represents the points on the graph at which the number of embryo variant alleles shared with the maternal source would be equal to the number of embryo variant alleles shared with the paternal source for each chromosome.

DNA extracted from a human embryo having a known karyotype 68;XXY;mos28.2%–19 and DNA samples from both parents were sequenced and analyzed as described in Example 1. FIG. 7 shows a graph of the number of embryo variant alleles shared with paternal source (OvP) vs. the number of embryo variant alleles shared with maternal source (OvM) for each of the 23 chromosomes (blue dots). The dotted diagonal line represents the points on the graph at which the number of embryo variant alleles shared with the maternal source would be equal to the number of embryo variant alleles shared with the paternal source for each chromosome. Dots located above the diagonal line represent chromosomes for which there were more variant alleles shared between the embryo and father than between the embryo and mother. Dots located below the diagonal line represent chromosomes for which there were more variant alleles shared between the embryo and mother than between the embryo and father. As shown in the graph in FIG. 7, all dots are well below the diagonal line. The global shift towards higher maternal contribution of alleles shown in FIG. 7 supports a finding of polyploidy that is likely maternal in origin.

Figure 10A:
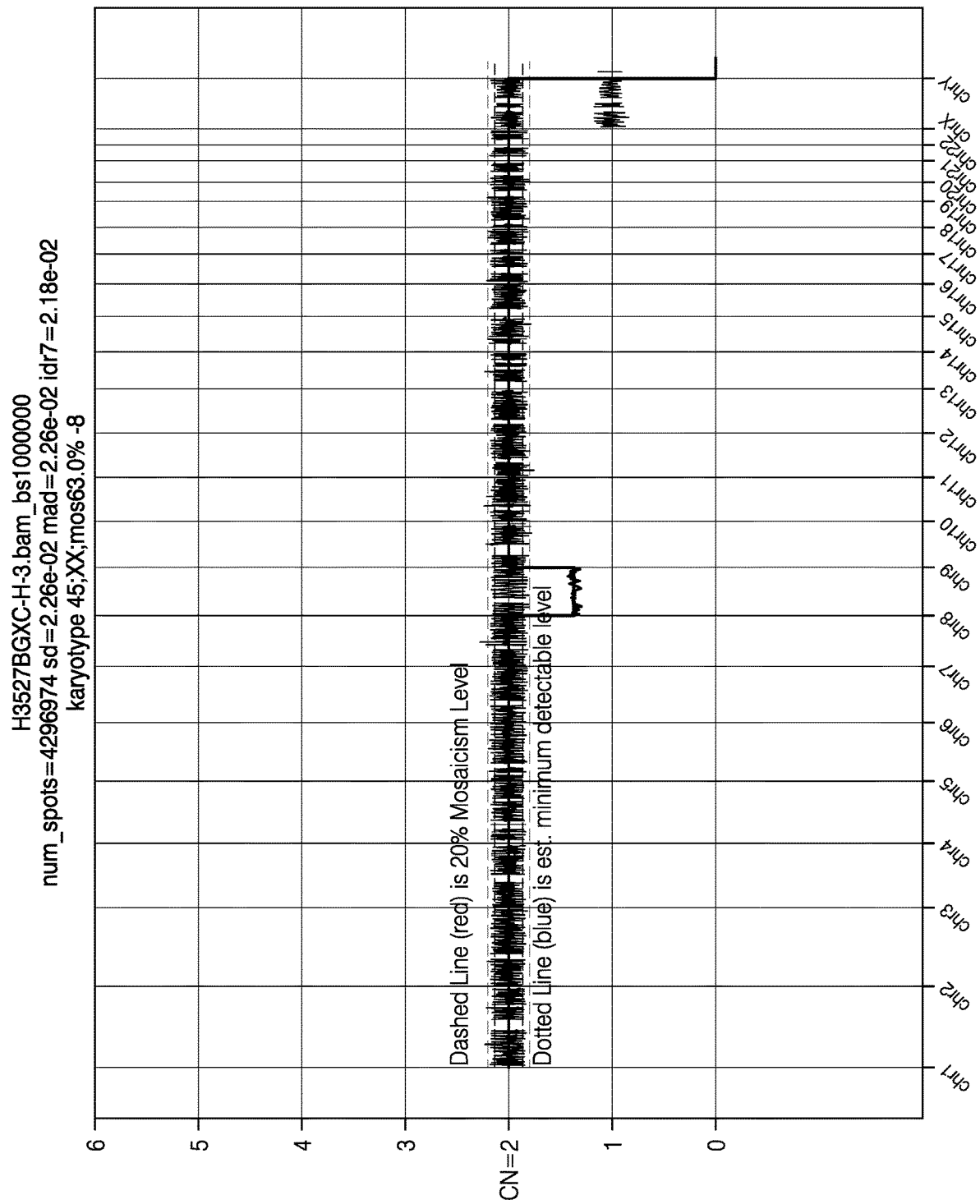
FIG. 10 depicts the results of chromosome copy number variation (CNV) analysis (FIG. 10A) and pattern of inheritance analysis (FIG. 10B; chromosome dose chart) for a triploid embryo determined to have a karyotype of 68,XXX; −8 with triploidy being of maternal origin, in accordance with various embodiments.
Figure 10B:
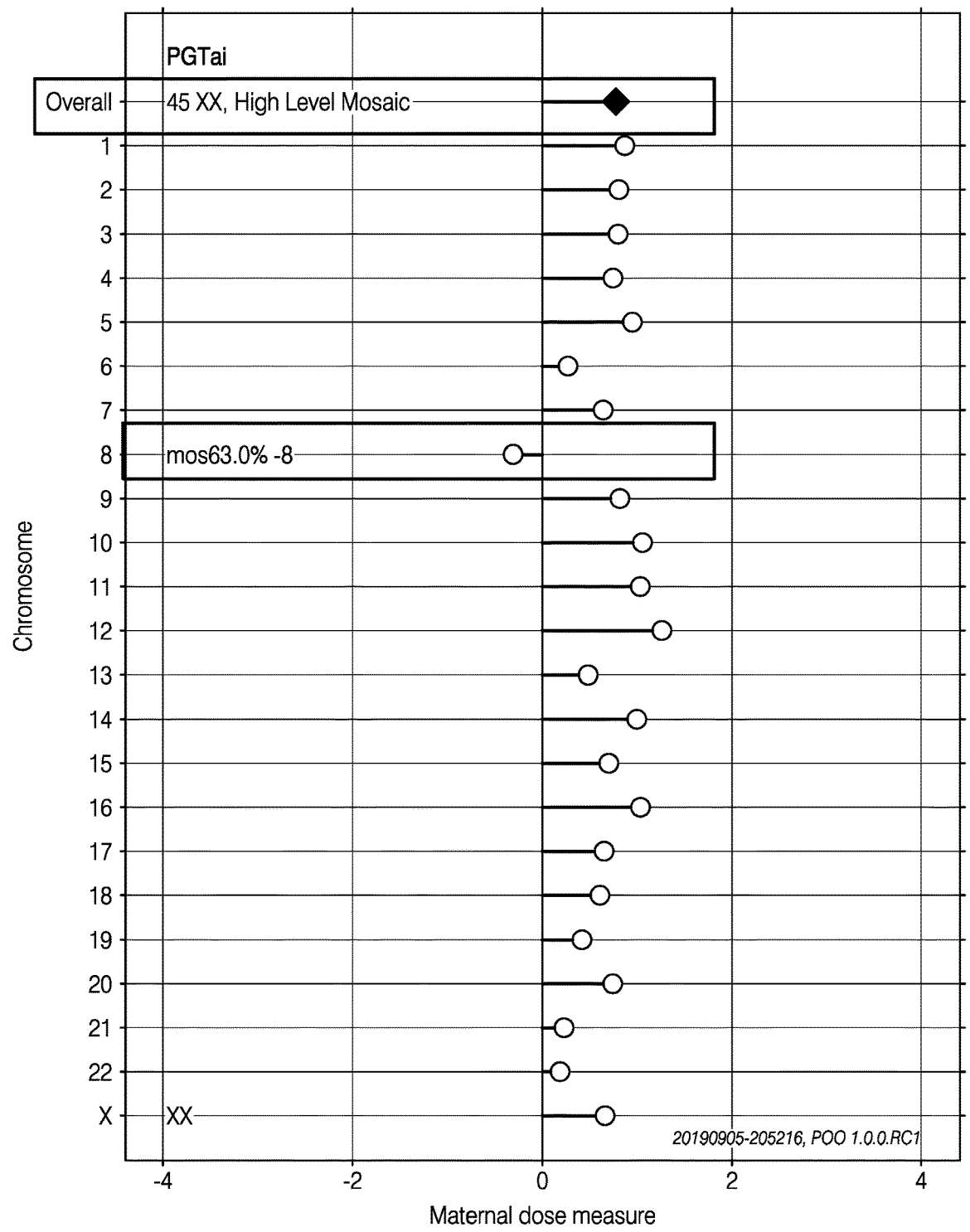

In another example, CNV analysis (conducted using methods described herein) of DNA from a trophectoderm biopsy of a human embryo that were sequenced at 0.1× coverage determined that the embryo was a female and had a loss of chromosome 8. FIG. 10A shows the results of the CNV analysis as a graph of chromosome copy number (CN) on the y-axis for each chromosome (listed on the x-axis) illustrating the deviation from a CN of 2 for chromosome 8. The DNA of the embryo and both parents (sequenced at 0.1×) were analyzed essentially as described in Example 1 and using methods described herein to assess ploidy and pattern of inheritance. The results of the analysis are depicted in the form of a chromosome dose chart in FIG. 10B with chromosome number listed vertically and maternal dose measure on the x-axis. Chromosome dose is a relative measure of the relatedness of the maternal vs paternal samples to the embryo, expressed on a log 2 scale. Positive values indicate a stronger relationship between the embryo and the mother; negative values indicate a stronger relationship between the embryo and the father. As shown in FIG. 10B, the results identified a genome-wide maternal dosage imbalance in the embryo indicating the embryo has additional genetic matter from the mother. The loss of chromosome 8, while not called because of preference given to genome-wide gains, appears to be maternal (blue box in FIG. 10B) as the dosage chart suggests 1 copy of chromosome 8 from the mother and 1 copy of chromosome 8 from the father is present. Based on these results, the embryo is reported as 68,XXX; –8 with the origin of triploidy being maternal.

Example 5—Classification of Parental Origin of Partial Gain/Loss and Trisomy

Figure 11A:
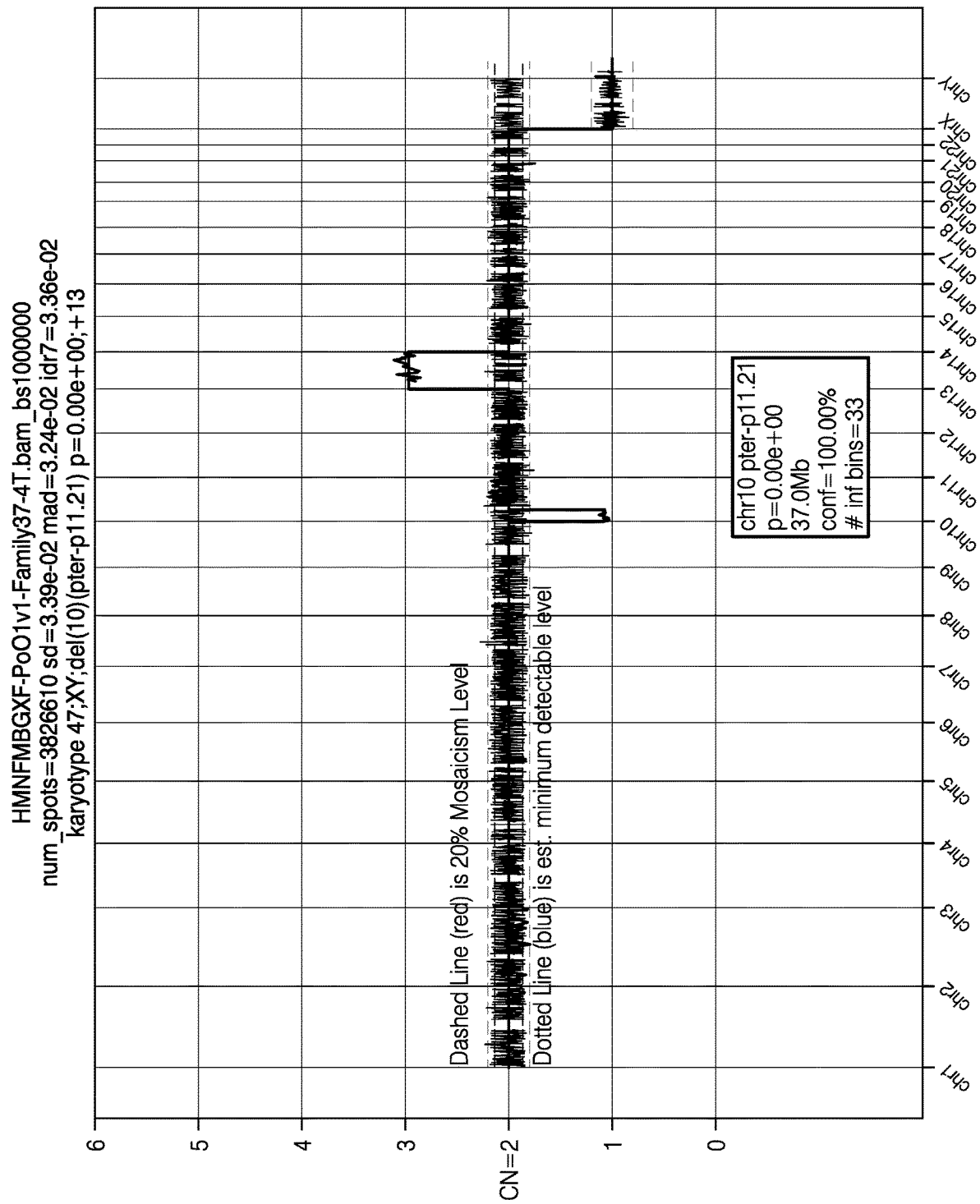
FIG. 11 depicts the results of CNV analysis (FIG. 11A) and pattern of inheritance analysis (FIG. 11B; chromosome dose chart) for an embryo determined to have a meiotic partial loss of chromosome 10 and a meiotic gain of chromosome 13 with a karyotype of 47;XY; del(10)(pter-p11.21) (paternal), +13 (maternal), in accordance with various embodiments.
Figure 11B:
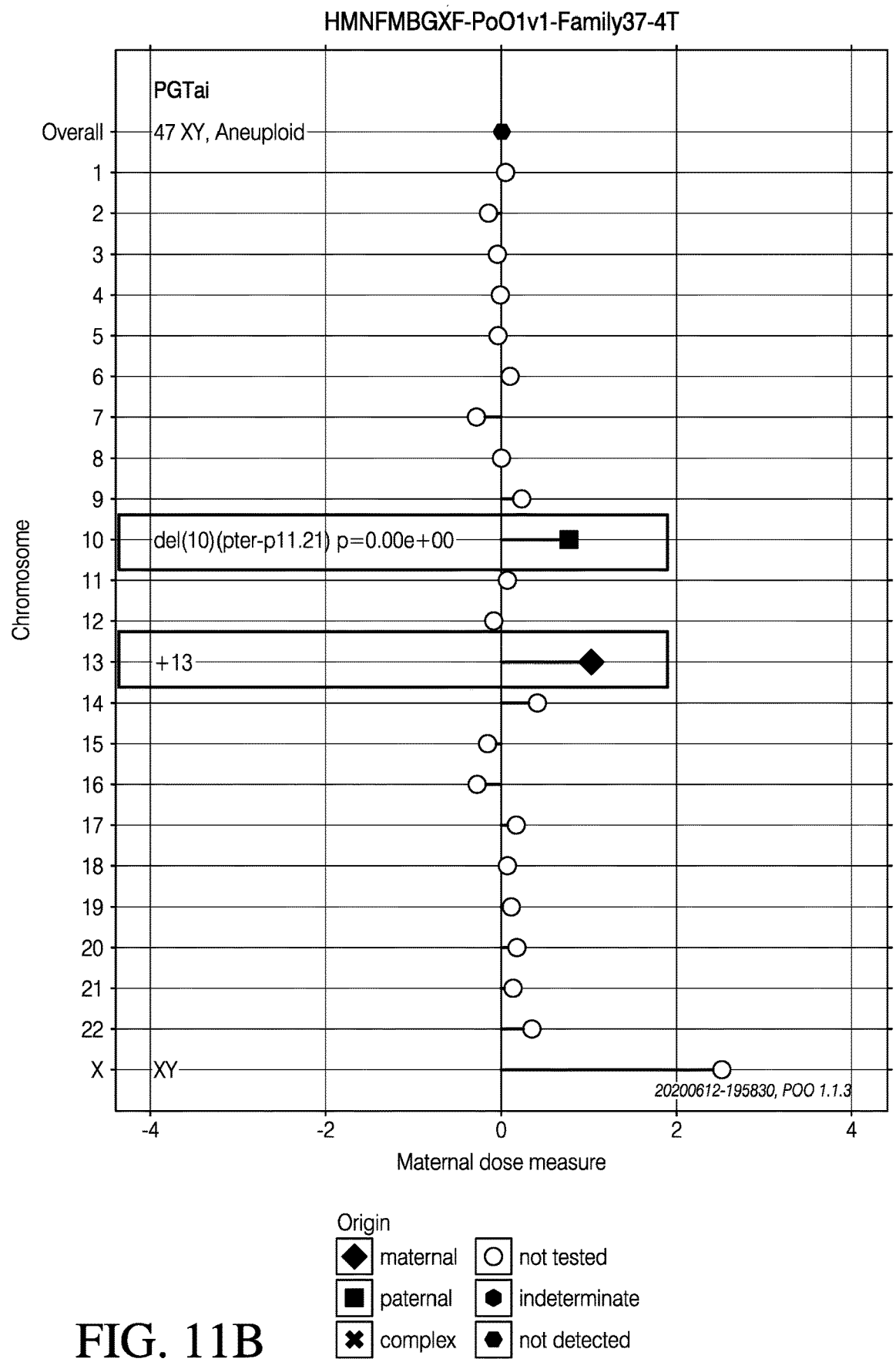

CNV analysis (conducted using methods described herein) of DNA from a trophectoderm biopsy of a human embryo that were sequenced at 0.1× coverage determined that the embryo was a male and contained a partial loss of chromosome 10 and a meiotic gain of chromosome 13. FIG. 11A shows the results of the CNV analysis as a graph of chromosome copy number (CN) on the y-axis for each chromosome (listed on the x-axis) illustrating the deviation from a CN of 2 for chromosomes 10 and 13. The DNA of the embryo and both parents (sequenced at 0.1×) were analyzed essentially as described in Example 1 and using methods described herein to assess pattern of inheritance. The results of the analysis are depicted in the form of a chromosome dose chart in FIG. 11B with chromosome number listed vertically and maternal dose measure on the x-axis. As shown in FIG. 11B, the results of the analysis identified that the loss of the short arm of chromosome 10 was of paternal origin (red box) and the gain of chromosome 13 was of maternal origin (blue box). Thus, the final result for this embryo is 47;XY; del(10)(pter-p11.21) (paternal), +13 (maternal).

Example 6—Classification of Parental Origin of Monosomy

Figure 12A:
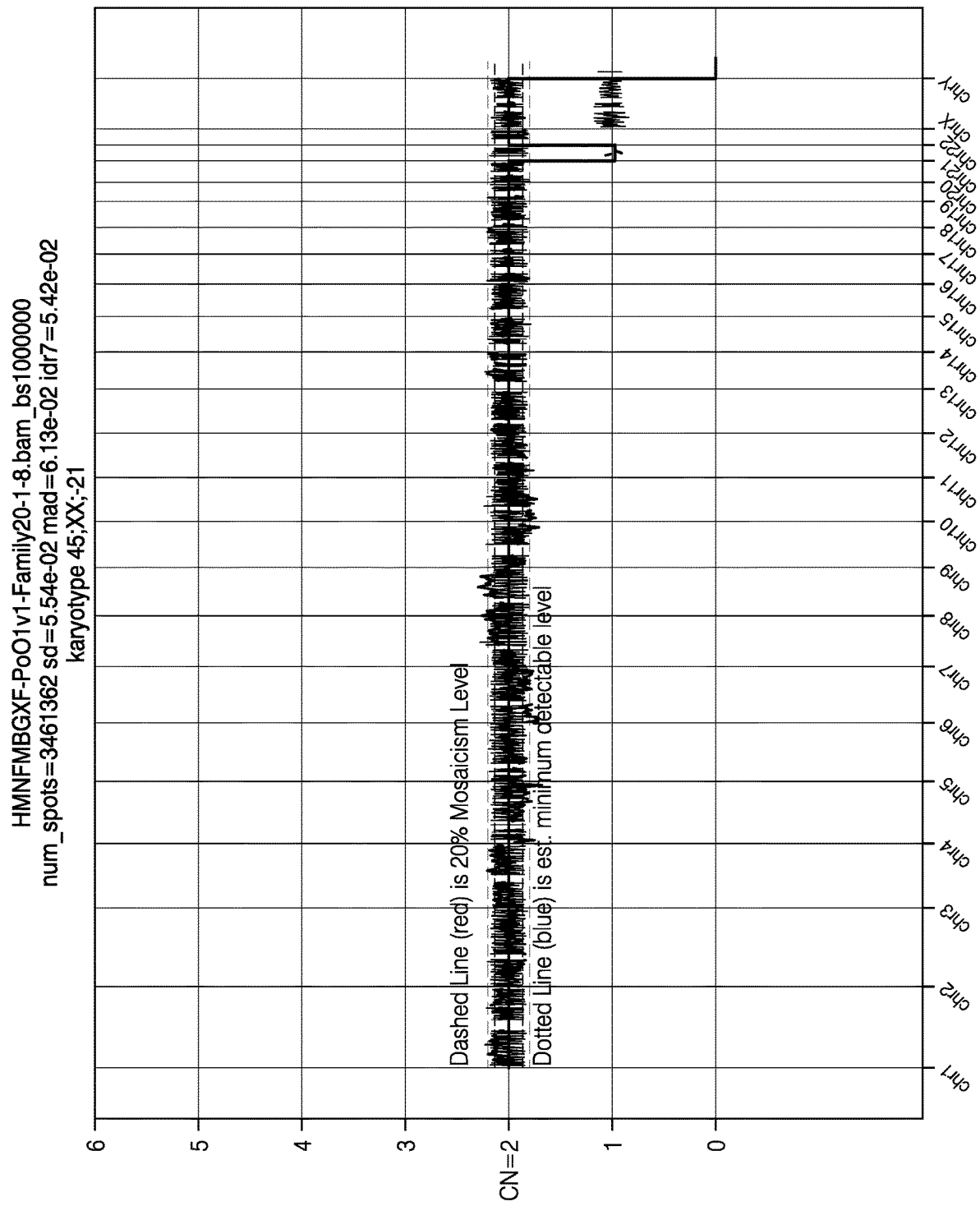
FIG. 12 depicts the results of CNV analysis (FIG. 12A) and pattern of inheritance analysis (FIG. 12B; chromosome dose chart) for an embryo determined to have a karyotype of 45,XX; −21 with monosomy being maternal, in accordance with various embodiments.
Figure 12B:
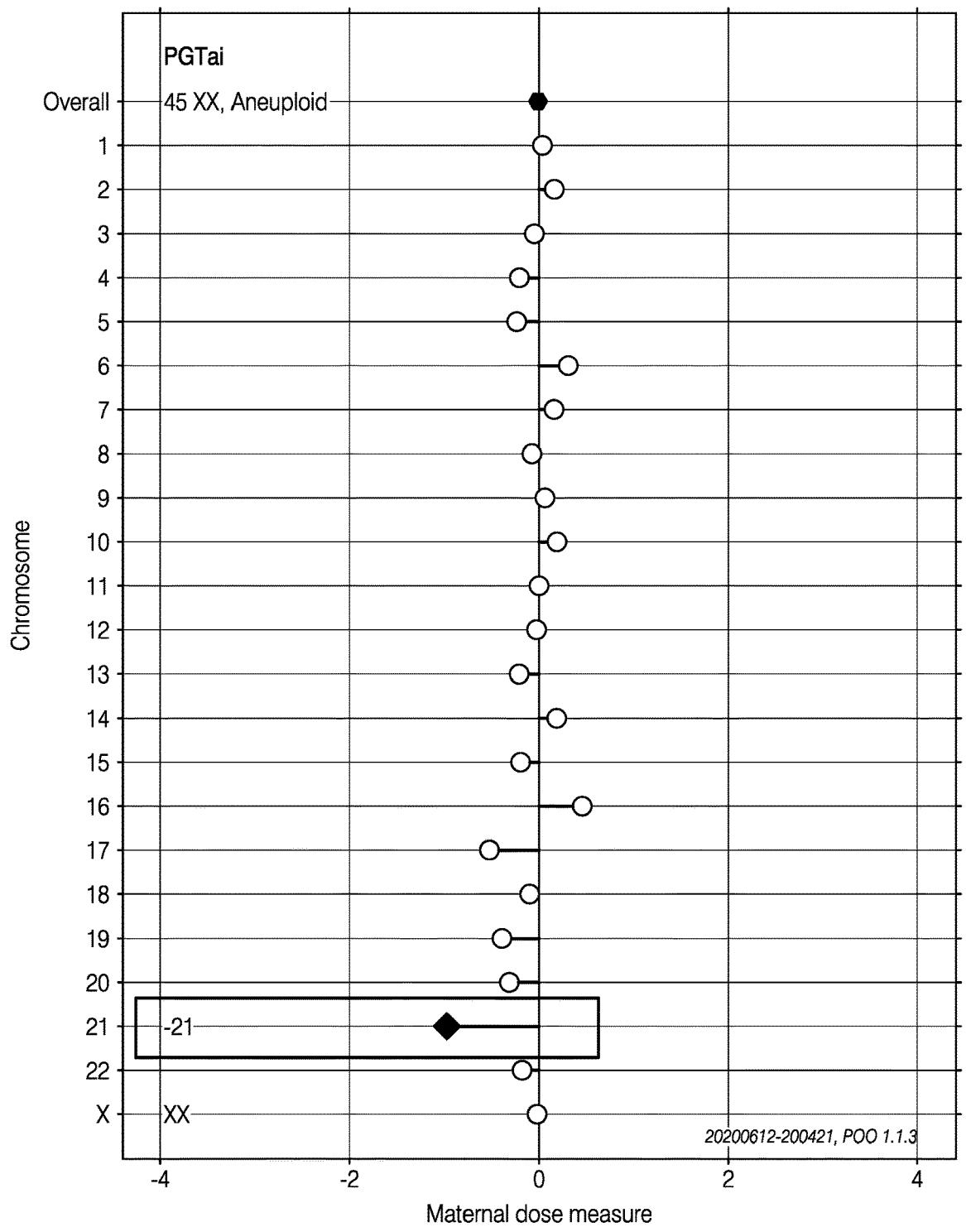

CNV analysis (conducted using methods described herein) of DNA from a trophectoderm biopsy of a human embryo that were sequenced at 0.1× coverage determined that the embryo was a male and contained a meiotic loss of chromosome 21. FIG. 12A shows the results of the CNV analysis as a graph of chromosome copy number (CN) on the y-axis for each chromosome (listed on the x-axis) illustrating the deviation from a CN of 2 for chromosome 21. The DNA of the embryo and both parents (sequenced at 0.1×) were analyzed essentially as described in Example 1 and using methods described herein to assess pattern of inheritance. The results of the analysis are depicted in the form of a chromosome dose chart in FIG. 12B with chromosome number listed vertically and maternal dose measure on the x-axis. As shown in FIG. 12B, the results of the analysis identified that the loss of chromosome 21 was of maternal origin (blue box). Thus, the final result for this embryo is 45;XX; −21 (maternal).

Example 7—Supporting Clinical Data with SNP Array (Gold Standard Truth)

A total of 65 embryos having meiotic aneuploidies previously assessed for parent of origin by the gold standard SNP array technology were interrogated utilizing ultra-low pass sequencing methods for pattern of inheritance determination as described herein. 65/65 aneuploidies interrogated via the pattern of inheritance method described herein produced the expected inheritance patterns (see Table 1). This data set includes all form of meiotic aneuploidies including whole chromosome gains and losses, partial gains and losses and genome-wide chromosome gains (polyploidy).

TABLE 1

SNP Array and Pattern of Inheritance Assessment
Comparison Results for Tests of 65 Embryos

| | | SNP ARRAY RESULT (Gold Standard Truth) | | |
|---|---|---|---|---|
| | | Maternal Origin | Paternal Origin | Euploid (none) |
| PATTERN OF INHERITANCE METHOD OF ANALYSIS (embodiments described herein) | Maternal Origin | 48 | | |
| | Paternal Origin | | 17 | |
| | Euploid (none) | | | 12 |

Computer Implemented System

In various embodiments, the methods for determining pattern of inheritance in an embryo for a region of interest can be implemented via computer software or hardware. That is, as depicted in FIG. 8, the methods disclosed herein can be implemented on a computing device 830 that includes a region of interest engine (ROI engine) 840, a single nucleotide polymorphism identification engine (SNP identification engine) 850, an imputation engine 860, and a pattern of inheritance engine (POI engine) 870. In various embodiments, the computing device 830 can be communicatively connected to a data store 810 and a display device 880 via a direct connection or through an internet connection.

It should be appreciated that the various engines depicted in FIG. 8 can be combined or collapsed into a single engine, component or module, depending on the requirements of the particular application or system architecture. Moreover, in various embodiments, the region of interest engine (ROI engine) 840, the single nucleotide polymorphism identification engine (SNP identification engine) 850, the imputation engine 860, and the pattern of inheritance engine (POI engine) 870 can comprise additional engines or components as needed by the particular application or system architecture.

Figure 13:
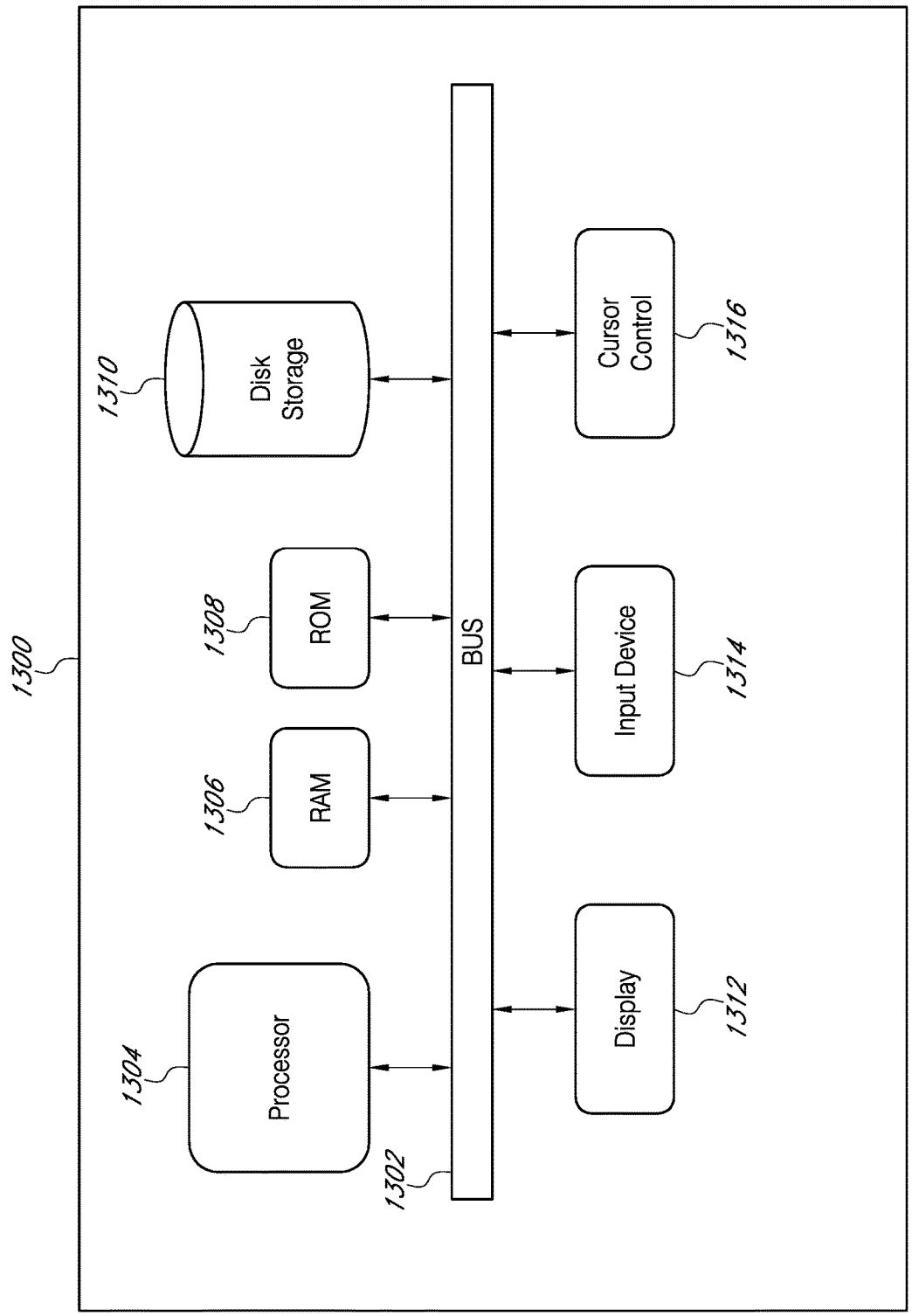
FIG. 13 is a block diagram illustrating a computer system for use in performing methods provided herein, in accordance with various embodiments.

FIG. 13 is a block diagram illustrating a computer system 1300 upon which embodiments of the present teachings may be implemented. In various embodiments of the present teachings, computer system 1300 can include a bus 1302 or other communication mechanism for communicating information and a processor 1304 coupled with bus 1302 for processing information. In various embodiments, computer system 1300 can also include a memory, which can be a random-access memory (RAM) 1306 or other dynamic storage device, coupled to bus 1302 for determining instructions to be executed by processor 1304. Memory can also be used for storing temporary variables or other intermediate information during execution of instructions to be executed by processor 1304. In various embodiments, computer system 1300 can further include a read only memory (ROM) 1308 or other static storage device coupled to bus 1302 for storing static information and instructions for processor 1304. A storage device 1310, such as a magnetic disk or optical disk, can be provided and coupled to bus 1302 for storing information and instructions.

In various embodiments, computer system 1300 can be coupled via bus 1302 to a display 1312, such as a cathode ray tube (CRT) or liquid crystal display (LCD), for displaying information to a computer user. An input device 1314, including alphanumeric and other keys, can be coupled to bus 1302 for communication of information and command selections to processor 1304. Another type of user input device is a cursor control 1316, such as a mouse, a trackball or cursor direction keys for communicating direction information and command selections to processor 1304 and for controlling cursor movement on display 1312. This input device 1314 typically has two degrees of freedom in two axes, a first axis (i.e., x) and a second axis (i.e., y), that allows the device to specify positions in a plane. However, it should be understood that input devices 1314 allowing for 3-dimensional (x, y and z) cursor movement are also contemplated herein.

Consistent with certain implementations of the present teachings, results can be provided by computer system 1300 in response to processor 1304 executing one or more sequences of one or more instructions contained in memory 1306. Such instructions can be read into memory 1306 from another computer-readable medium or computer-readable storage medium, such as storage device 1310. Execution of the sequences of instructions contained in memory 1306 can cause processor 1304 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1304 for execution. Such a medium can take many forms, including but not limited to, non-volatile media, volatile media, and transmission media. Examples of non-volatile media can include, but are not limited to, dynamic memory, such as memory 1306. Examples of transmission media can include, but are not limited to, coaxial cables, copper wire, and fiber optics, including the wires that comprise bus 1302.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, another memory chip or cartridge, or any other tangible medium from which a computer can read.

In addition to computer-readable medium, instructions or data can be provided as signals on transmission media included in a communications apparatus or system to provide sequences of one or more instructions to processor 1304 of computer system 1300 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein, flow charts, diagrams and accompanying disclosure can be implemented using computer system 1000 as a standalone device or on a distributed network or shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1300, whereby processor 1304 would execute the analyses and determinations provided by these engines, subject to instructions provided by any one of, or a combination of, memory components 1306/1308/1310 and user input provided via input device 1314.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

Recitation of Embodiments

Embodiment 1: A method for determining pattern of inheritance in an embryo for a region of interest, comprising:

receiving embryo, maternal and paternal sequence data, wherein the maternal sequence data is from a mother of the embryo and the paternal sequence data is from a father of the embryo;

aligning the received sequence data to a reference genome;

identifying a region of interest in the aligned embryo sequence data;

identifying single nucleotide polymorphisms (SNPs) in the maternal sequence data, paternal sequence data, and the identified region of interest in the embryo sequence data;

imputing missing gaps in the maternal sequence data and the paternal sequence data using an imputation reference;

counting the number of SNPs that are common between the embryo and the mother in the identified region of interest for the embryo sequence data and a corresponding region on the maternal sequence data to determine a maternal contribution value;

counting the number of SNPs that are common between the embryo and the father in the identified region of interest for the embryo sequence data and a corresponding region on the paternal sequence data to determine a paternal contribution value; and classifying a pattern of inheritance for the embryo as maternal or paternal based on the relative contribution values between mother and father.

Embodiment 2: The method of Embodiment 1, further comprising counting SNPs across the entire genome to determine the maternal and paternal contribution values and determine if the embryo is polyploid.

Embodiment 3: The method of Embodiment 2, wherein for an embryo that is polyploid, the method further comprising classifying a pattern of inheritance for the polyploid as maternal or paternal based on the relative contribution values between mother and father.

Embodiment 4: The method of any of Embodiments 1 to 3, wherein at least one of the embryo, maternal and paternal sequence data is acquired by low-coverage sequencing.

Embodiment 5: The method of Embodiment 4, wherein the low-coverage sequencing is between about 0.001 and 10×.

Embodiment 6: The method of Embodiment 4, wherein the low-coverage sequencing is between about 0.01 and 0.5×.

Embodiment 7: The method of Embodiment 4, wherein the low-coverage sequencing is between about 0.25 and 0.2×.

Embodiment 8: The method of any one of Embodiments 1 to 7, wherein the region of interest is genome wide.

Embodiment 9: The method of any one of Embodiments 1 to 8, wherein the region of interest is a copy number variation.

Embodiment 10: The method of any one of Embodiments 1 to 9, wherein the imputation reference comprises at least 1000 genomes.

Embodiment 11: The method of any one of Embodiments 1 to 10, further comprising filtering at least one of the embryo, maternal and paternal sequencing data to remove sequencing artifacts.

Embodiment 12: The method of Embodiment 11, wherein the filtering comprises excluding sequences of sites with any missing alleles between the embryo, mother and father.

Embodiment 13: The method of Embodiment 11, wherein the filtering comprises excluding sequences of sites with constant alleles across between the embryo, mother and father.

Embodiment 14: The method of Embodiment 11, wherein the filtering comprises excluding sequences of sites with a novel allele within one of the embryo, mother and father.

Embodiment 15: The method of Embodiment 11, wherein the filtering comprises excluding SNPs that are inconsistent with Mendelian inheritance.

Embodiment 16: A non-transitory computer-readable medium storing computer instructions for determining pattern of inheritance in an embryo for a region of interest, comprising:
  receiving embryo, maternal and paternal sequence data, wherein the maternal sequence data is from a mother of the embryo and the paternal sequence data is from a father of the embryo;
  aligning the received sequence data to a reference genome;
  identifying a region of interest in the aligned embryo sequence data;
  identifying single nucleotide polymorphisms (SNPs) in the maternal sequence data, paternal sequence data, and the identified region of interest in the embryo sequence data;
  imputing missing gaps in the maternal sequence data and the paternal sequence data using an imputation reference;
  counting the number of SNPs that are common between the embryo and the mother in the identified region of interest for the embryo sequence data and a corresponding region on the maternal sequence data to determine a maternal contribution value;
  counting the number of SNPs that are common between the embryo and the father in the identified region of interest for the embryo sequence data and a corresponding region on the paternal sequence data to determine a paternal contribution value; and
  classifying a pattern of inheritance for the embryo as maternal or paternal based on the relative contribution values between mother and father.

Embodiment 17: The method of Embodiment 16, further comprising counting SNPs across the entire genome to determine the maternal and paternal contribution values and determine if the embryo is polyploid.

Embodiment 18: The method of Embodiment 17, wherein for an embryo that is polyploid, the method further comprising classifying a pattern of inheritance for the polyploid as maternal or paternal based on the relative contribution values between mother and father.

Embodiment 19: The method of any of Embodiments 16 to 18, wherein at least one of the embryo, maternal and paternal sequence data is acquired by low-coverage sequencing.

Embodiment 20: The method of Embodiment 19, wherein the low-coverage sequencing is between about 0.001 and 10×.

Embodiment 21: The method of Embodiment 19, wherein the low-coverage sequencing is between about 0.01 and 0.5×.

Embodiment 22: The method of Embodiment 19, wherein the low-coverage sequencing is between about 0.25 and 0.2×.

Embodiment 23: The method of Embodiment 19, wherein the region of interest is genome wide.

Embodiment 24: The method of any of Embodiments 16 to 23, wherein the region of interest is a copy number variation.

Embodiment 25: The method of any of Embodiments 16 to 24, wherein the imputation reference comprises at least 1000 genomes.

Embodiment 26: The method of any of Embodiments 16 to 25, further comprising filtering at least one of the embryo, maternal and paternal sequencing data to remove sequencing artifacts.

Embodiment 27: The method of Embodiment 26, wherein the filtering comprises excluding sequences of sites with any missing alleles between the embryo, mother and father.

Embodiment 28: The method of Embodiment 26, wherein the filtering comprises excluding sequences of sites with constant alleles across between the embryo, mother and father.

Embodiment 29: The method of Embodiment 26, wherein the filtering comprises excluding sequences of sites with a novel allele within one of the embryo, mother and father.

Embodiment 30: The method of Embodiment 26, wherein the filtering comprises excluding SNPs that are inconsistent with Mendelian inheritance.

Embodiment 31: A system for determining pattern of inheritance in an embryo for a region of interest, comprising:
  a data store for receiving embryo, maternal and paternal sequence data, wherein the maternal sequence data is from a mother of the embryo and the paternal sequence data is from a father of the embryo;
  a computing device communicatively connected to the data store, the computing device comprising
    an ROI engine configured to align the received sequence data to a reference genome, and identify a region of interest in the aligned embryo sequence data;
    a SNP identification engine configure to identify single nucleotide polymorphisms (SNPs) in the maternal sequence data, paternal sequence data, and the identified region of interest in the embryo sequence data;
    an imputation engine configured to impute missing gaps in the maternal sequence data and the paternal sequence data using an imputation reference; and
    a POI engine configured to:
      count the number of SNPs that are common between the embryo and the mother in the identified region of interest for the embryo sequence data and a corresponding region on the maternal sequence data to determine a maternal contribution value;
      count the number of SNPs that are common between the embryo and the father in the identified region of interest for the embryo sequence data and a corresponding region on the paternal sequence data to determine a paternal contribution value; and
      classify a pattern of inheritance for the embryo as maternal or paternal based on the relative contribution values between mother and father;
  and
  a display communicatively connected to the computing device and configured to display a report containing the classified pattern of inheritance for the embryo.

Embodiment 32: The system of Embodiment 31, wherein the POI engine is further configured to count SNPs across the entire genome to determine the maternal and paternal contribution values and determine if the embryo is polyploid.

Embodiment 33: The system of Embodiments 31 or 32, wherein for an embryo that is polyploid, the POI engine is further configured to classify a pattern of inheritance for the polyploid as maternal or paternal based on the relative contribution values between mother and father.

Embodiment 34: The system of any one of Embodiments 31 to 33, wherein at least one of the embryo, maternal and paternal sequence data is acquired by low-coverage sequencing.

Embodiment 35: The system of Embodiment 34, wherein the low-coverage sequencing is between about 0.001 and 10×.

Embodiment 36: The system of Embodiment 34, wherein the low-coverage sequencing is between about 0.01 and 0.5×.

Embodiment 37: The system of Embodiment 34, wherein the low-coverage sequencing is between about 0.25 and 0.2×.

Embodiment 38: The system of any one of Embodiments 31 to 37, wherein the region of interest is genome wide.

Embodiment 39: The system of any one of Embodiments 31 to 37, wherein the region of interest is a copy number variation.

Embodiment 40: The system of any one of Embodiments 31 to 39, wherein the imputation reference comprises at least 1000 genomes.

Embodiment 41: The system of any one of Embodiments 31 to 40, wherein the imputation engine is further configured to filter at least one of the embryo, maternal and paternal sequencing data to remove sequencing artifacts.

Embodiment 42: The system of Embodiment 41, wherein the filtering comprises excluding sequences of sites with any missing alleles between the embryo, mother and father.

Embodiment 43: The system of Embodiment 41, wherein the filtering comprises excluding sequences of sites with constant alleles across between the embryo, mother and father.

Embodiment 44: The system of Embodiment 41, wherein the filtering comprises excluding sequences of sites with a novel allele within one of the embryo, mother and father.

Embodiment 45: The system of Embodiment 41, wherein the filtering comprises excluding SNPs that are inconsistent with Mendelian inheritance.

What is claimed:

1. A method for determining pattern of inheritance in an embryo for a region of interest, comprising:
    receiving low-coverage embryo, maternal and paternal sequence data, wherein the maternal sequence data is from a mother of the embryo and the paternal sequence data is from a father of the embryo, and wherein the embryo, maternal and paternal sequence data are between 0.001× and 10×;
    aligning the received sequence data to a reference genome;
    identifying a region of interest in the aligned embryo sequence data;
    identifying single nucleotide polymorphisms (SNPs) in the maternal sequence data, paternal sequence data, and the identified region of interest in the embryo sequence data;
    imputing missing gaps in the maternal sequence data and the paternal sequence data using an imputation reference;
    counting a first number of SNPs that are common between the embryo and the mother in the identified region of interest for the embryo sequence data and a corresponding region on the maternal sequence data to determine a maternal contribution value, designated OvM, based on the first count;
    counting a second number of SNPs that are common between the embryo and the father in the identified region of interest for the embryo sequence data and a corresponding region on the paternal sequence data to determine a paternal contribution value, designated OvP, based on the second count;
    calculating a statistic describing the relative contribution values between mother and father according to the following formula: log2

$$\left( \frac{(OvM) + s}{(OvP) + s} \right),$$

wherein s is a smoothing parameter; and
    classifying a pattern of inheritance for the embryo as maternal or paternal based on the statistic.

2. The method of claim 1, further comprising counting SNPs across the entire genome to determine the maternal and paternal contribution values and determine if the embryo is polyploid.

3. The method of claim 2, wherein for an embryo that is polyploid, the method further comprising classifying a pattern of inheritance for the polyploid as maternal or paternal based on the relative contribution values between mother and father.

4. The method of claim 1, wherein the low-coverage sequencing is between about 0.01 and 0.5×.

5. The method of claim 1, wherein the low-coverage sequencing is between about 0.2 and 0.25×.

6. A non-transitory computer-readable medium storing computer instructions for determining pattern of inheritance in an embryo for a region of interest, comprising:
    receiving low-coverage embryo, maternal and paternal sequence data, wherein the maternal sequence data is from a mother of the embryo and the paternal sequence data is from a father of the embryo, and wherein the embryo, maternal and paternal sequence data are between 0.001× and 10×;
    aligning the received sequence data to a reference genome;
    identifying a region of interest in the aligned embryo sequence data;
    identifying single nucleotide polymorphisms (SNPs) in the maternal sequence data, paternal sequence data, and the identified region of interest in the embryo sequence data;
    imputing missing gaps in the maternal sequence data and the paternal sequence data using an imputation reference;
    counting a first number of SNPs that are common between the embryo and the mother in the identified region of interest for the embryo sequence data and a corresponding region on the maternal sequence data to determine a maternal contribution value, designated OvM, based on the first count;
    counting a second number of SNPs that are common between the embryo and the father in the identified region of interest for the embryo sequence data and a corresponding region on the paternal sequence data to determine a paternal contribution value, designated OvP, based on the second count;

calculating a statistic describing the relative contribution values between mother and father according to the following formula: log2

$$\left(\frac{(OvM)+s}{(OvP)+s}\right),$$

wherein s is a smoothing parameter; and classifying a pattern of inheritance for the embryo as maternal or paternal based on the statistic.

7. The method of claim 6, further comprising counting SNPs across the entire genome to determine the maternal and paternal contribution values and determine if the embryo is polyploid.

8. The method of claim 7, wherein for an embryo that is polyploid, the method further comprising classifying a pattern of inheritance for the polyploid as maternal or paternal based on the relative contribution values between mother and father.

9. The method of claim 6, wherein the low-coverage sequencing is between about 0.01 and 0.5×.

10. The method of claim 6, wherein the low-coverage sequencing is between about 0.2 and 0.25×.

11. A system for determining pattern of inheritance in an embryo for a region of interest, comprising:

a data store for receiving low-coverage embryo, maternal and paternal sequence data, wherein the maternal sequence data is from a mother of the embryo and the paternal sequence data is from a father of the embryo, and wherein the embryo, maternal and paternal sequence data are between 0.001× and 10×;

a computing device communicatively connected to the data store, the computing device comprising an ROI engine configured to align the received sequence data to a reference genome, and identify a region of interest in the aligned embryo sequence data;

a SNP identification engine configured to identify single nucleotide polymorphisms (SNPs) in the maternal sequence data, paternal sequence data, and the identified region of interest in the embryo sequence data;

an imputation engine configured to impute missing gaps in the maternal sequence data and the paternal sequence data using an imputation reference; and a POI engine configured to:

count the first number of SNPs that are common between the embryo and the mother in the identified region of interest for the embryo sequence data and a corresponding region on the maternal sequence data to determine a maternal contribution value, designated OvM, based on the first count;

count the second number of SNPs that are common between the embryo and the father in the identified region of interest for the embryo sequence data and a corresponding region on the paternal sequence data to determine a paternal contribution value, designated OvP, based on the second count;

calculating a statistic describing the relative contribution values between mother and father according to the following formula:

$$\log2\left(\frac{(OvM)+s}{(OvP)+s}\right),$$

wherein s is a smoothing parameter; and classify a pattern of inheritance for the embryo as maternal or paternal based on the statistic; and a display communicatively connected to the computing device and configured to display a report containing the classified pattern of inheritance for the embryo.

12. The system of claim 11, wherein the POI engine is further configured to count SNPs across the entire genome to determine the maternal and paternal contribution values and determine if the embryo is polyploid.

13. The system of claim 12, wherein for an embryo that is polyploid, the POI engine is further configured to classify a pattern of inheritance for the polyploid as maternal or paternal based on the relative contribution values between mother and father.

14. The system of claim 11, wherein the low-coverage sequencing is between about 0.01 and 0.5×.

* * * * *

UNITED STATES PATENT AND TRADEMARK OFFICE
CERTIFICATE OF CORRECTION

PATENT NO. : 12,176,069 B2
APPLICATION NO. : 16/907074
DATED : December 24, 2024
INVENTOR(S) : John Burke et al.

Page 1 of 1

It is certified that error appears in the above-identified patent and that said Letters Patent is hereby corrected as shown below:

In the Claims

<u>Column 33</u>
Line 53, in Claim 1, delete "0.001×and" and insert -- 0.001× and --

<u>Column 34</u>
Line 44, in Claim 6, delete "0.001×and" and insert -- 0.001× and --

<u>Column 35</u>
Line 14 (Approx.), in Claim 7, delete "The method of claim 6," and insert -- The non-transitory computer-readable medium of claim 6, --
Line 18 (Approx.), in Claim 8, delete "The method of claim 7," and insert -- The non-transitory computer-readable medium of claim 7, --
Line 23 (Approx.), in Claim 9, delete "The method of claim 6," and insert -- The non-transitory computer-readable medium of claim 6, --
Line 25 (Approx.), in Claim 10, delete "The method of claim 6," and insert -- The non-transitory computer-readable medium of claim 6, --
Line 34 (Approx.), in Claim 11, delete "0.001×and" and insert -- 0.001× and --

Signed and Sealed this
Eleventh Day of March, 2025

Coke Morgan Stewart
*Acting Director of the United States Patent and Trademark Office*